(12) United States Patent
Van Rooijen et al.

(10) Patent No.: US 7,531,325 B2
(45) Date of Patent: May 12, 2009

(54) METHOD FOR CLEAVAGE OF FUSION PROTEINS

(75) Inventors: Gijs Van Rooijen, Calgary (CA); Joenel Alcantara, Calgary (CA); Maurice M. Moloney, Calgary (CA)

(73) Assignee: SemBioSys Genetics Inc., Calgary, Alberta (CA)

( * ) Notice: Subject to any disclaimer, the term of this patent is extended or adjusted under 35 U.S.C. 154(b) by 0 days.

(21) Appl. No.: 10/322,746

(22) Filed: Dec. 19, 2002

(65) Prior Publication Data

US 2003/0166162 A1 Sep. 4, 2003

Related U.S. Application Data

(63) Continuation-in-part of application No. 09/402,488, filed as application No. PCT/CA98/00398 on Apr. 23, 1998.

(60) Provisional application No. 60/044,254, filed on Apr. 25, 1997.

(51) Int. Cl.
*C12P 21/04* (2006.01)
*C12P 21/06* (2006.01)
*C12P 21/00* (2006.01)

(52) U.S. Cl. .................. 435/69.7; 435/69.1; 800/4; 800/7

(58) Field of Classification Search ............... 435/69.1, 435/69.7, 212, 71.1, 71.2, 70.1, 70.3
See application file for complete search history.

(56) References Cited

U.S. PATENT DOCUMENTS

| 4,743,679 | A |   | 5/1988 | Cohen et al. |           |
|-----------|---|---|--------|--------------|-----------|
| 5,650,554 | A | * | 7/1997 | Moloney      | 800/288   |
| 6,265,204 | B1| * | 7/2001 | Ward et al.  | 435/254.11|

FOREIGN PATENT DOCUMENTS

| EP | 0 134 662 A1 | 3/1985 |
| WO | WO 91/11454  | 8/1991 |
| WO | WO 96/21029  | 7/1996 |

OTHER PUBLICATIONS

He et al. (1993) J Prot Chem 12:1-5.*
Walsh et al. (1996) J Biotechnol 45:235-241.*
"Current Protocols in Molecular Biology", John Wiley and Sons, Inc. New York, 1994, pp. 16.4.1 to 16.4.17.*
Yonezawa et al. (1996) Int J Pept Prot Res 47:56-61.*
Nedjar et al. (1991) Int J Biochem 23:377-381.*
Fine et al. (1993) Gen Comp Endocrinol 89:51-61.*
Branden et al. "Introduction to Protein Structure", Garland Publishing Inc., New York, p. 247.*
Witkowski et al. (1999) Biochemistry 38:11643-11650.*
Dang et al. (1999) Clin Cancer Res 5:471-474.*
Fox (2003) Nat Biotechnol 21:217.*
Dunn et al. "Aspartic Proteinases," Advances in Experimental Medicine and Biology, vol. 362, Plenum Press NY, 1995, pp. 1-9.*
Juengst (2003) BMJ 326:1410-1411.*
"Encyclopedia of Molecular Biology," Creighton, John Wiley and Sons, Inc., New York, 1999, pp. 2327-2328.*
Dyck et al. Trends Biotechnol 21:394-399, 2003.*
Vain et al. Theor Appl Genet 105:878-889, 2002.*
Potrykus Biotechnology 8:535-542, 1990.*
Houdebine, J Biotechnol 34:269-287, 1994.*
Sang, Mech. Dev., 121:1179-1186, 2004.*
Mozdziak, Dev. Dynam. 229:414-421, 2004.*
Mitalipov et al., Biol Reproduction 66:1367-1373, 2002.*
Koelsch, G. et al. 1994. Multiple functions of pro-parts of aspartic proteinase zymogens. FEBS Lett 343(1):6-10.
McCaman, M.T., and Cummings. 1986. A mutated bovine prochymosin zymogen can be activated without proteolytic processing at low pH. J Biol Chem. 261(33):15345-8.
Sekita, T., et al. 1975. Effect of 2-mercaptoethanol on cyanogen bromide cleavage of proteins. Keio J Med. 24(3):203-10.
Silen, J.L., Agard, D.A., 1989. The alpha-lytic protease pro-region does not require a physical linkage to activate the protease domain in vivo. Nature 341(6241):462-4.
Giam, C. et al. 1988. In Vivo and in Vitro Autoprocessing of Human Immunodeficiency Virus Protease Expressed in *Escherichia coli*. The Journal of Biological Chemistry 263(29): 14617-14620.
Hiramatsu, Ryuji et al., 1990. The Prepro-Peptide of *Mucor* Rennin Directs the Secretion of Human Growth Hormone by *Saccharomyces cerevisiae*. Applied and Environmental Microbiology vol. 56, No. 7: 2125-2132.
Nomura, N. et al. 1995. High level secretion by *Saccharomyces cerevisiae* of human apolipoprotein E as a fusion to Rhizomucor rennin. Biosci Biotechnol Biochem 59(3): 382-7.
Montgomery, D. S. et al. 1991. Expression of an Autoprocessing Cat-HIV-1 Proteinase Fusion Protein: Purification to Homogeneity of the Released 99 Residue Proteinase. Biochemical and Biophysical Research Communications, vol. 175, No. 3: 784-794.
Parmenter, D.L. et al. 1995. Production of biologically active hirudin in plant seeds using oleosin partitioning. Plant Molecular Biology 29: 1167-1180.
Blanka, K. et al. A Novel Method for Cleavage of Recombinant Fusion Proteins. 2002. SemiBioSys Genetics Inc. Abstract S28-17 and Poster presentation.
Cameron, Ewan R., "Recent Advanced in Transgenic Technology," Molecular Biotechnology, 7:253-265 (1997).

(Continued)

*Primary Examiner*—David J Steadman
(74) *Attorney, Agent, or Firm*—Bereskin & Parr; Micheline Gravelle

(57) ABSTRACT

An improved method for recovering recombinantly produced polypeptides is described. The method involves expressing the recombinant polypeptide as a fusion protein with a pro-peptide. The pro-peptide-polypeptide fusion protein can be cleaved and the recombinant polypeptide released under the appropriate conditions.

18 Claims, 19 Drawing Sheets

OTHER PUBLICATIONS

Montoliu, Lluis, "Gene Transfer Strategies in Animal Transgenesis," Cloning and Stem Cells, 4(1):39-46 (2002).

Ristevski, Sika, "Making Better Transgenic Models," Molecular Biotechnology 29:153-163 (2005).

Sigmund, Curt D., "Viewpoint: Are Studies in Genetically Altered Mice Out of Control?," Arterioscler Thromb Vasc Biol. 20:1425-1429 (2000).

Smith, Kevin R., "Gene Transfer in Higher Animals: Theoretical Considerations and Key Concepts," Journal of Biotechnology 99:1-22 (2002).

Examiner's Answer in co-pending U.S. Appl. No. 09/402,488 (55 pgs.), mailed Aug. 17, 2007.

* cited by examiner

FIGURE 1

Nucleotide sequence and the deduced amino acid sequence of a GST-Pro-Hirudin fusion.

```
1   ATG TCC CCT ATA CTA GGT TAT TGG AAA ATT AAG GGC CTT GTG CAA CCC ACT CGA CTT CTT    60
1   M   S   P   I   L   G   Y   W   K   I   K   G   L   V   Q   P   T   R   L   L   20

61  TTG GAA TAT CTT GAA GAA AAA TAT GAA GAG CAT TTG TAT GAG CGC GAT GAA GGT GAT AAA    120
21  L   E   Y   L   E   E   K   Y   E   E   H   L   Y   E   R   D   E   G   D   K    40

121 TGG CGA AAC AAA AAG TTT GAA TTG GGT TTG GAG TTT CCC AAT CTT CCT TAT TAT ATT GAT    180
41  W   R   N   K   K   F   E   L   G   L   E   F   P   N   L   P   Y   Y   I   D    60

181 GGT GAT GTT AAA TTA ACA CAG TCT ATG GCC ATC ATA CGT TAT ATA GCT GAC AAG CAC AAC    240
61  G   D   V   K   L   T   Q   S   M   A   I   I   R   Y   I   A   D   K   H   N    80

241 ATG TTG GGT GGT TGT CCA AAA GAG CGT GCA GAG ATT TCA ATG CTT GAA GGA GCG GTT TTG    300
81  M   L   G   G   C   P   K   E   R   A   E   I   S   M   L   E   G   A   V   L    100

301 GAT ATT AGA TAC GGT GTT TCG AGA ATT GCA TAT AGT AAA GAC TTT GAA ACT CTC AAA GTT    360
101 D   I   R   Y   G   V   S   R   I   A   Y   S   K   D   F   E   T   L   K   V    120

361 GAT TTT CTT AGC AAG CTA CCT GAA ATG CTG AAA ATG TTC GAA GAT CGT TTA TGT CAT AAA    420
121 D   F   L   S   K   L   P   E   M   L   K   M   F   E   D   R   L   C   H   K    140

421 ACA TAT TTA AAT GGT GAT CAT GTA ACC CAT CCT GAC TTC ATG TTG TAT GAC GCT CTT GAT    480
141 T   Y   L   N   G   D   H   V   T   H   P   D   F   M   L   Y   D   A   L   D    160

481 GTT GTT TTA TAC ATG GAC CCA ATG TGC CTG GAT GCG TTC CCA AAA TTA GTT TGT TTT AAA    540
161 V   V   L   Y   M   D   P   M   C   L   D   A   F   P   K   L   V   C   F   K    180

541 AAA CGT ATT GAA GCT ATC CCA CAA ATT GAT AAG TAC TTG AAA TCC AGC AAG TAT ATA GCA    600
181 K   R   I   E   A   I   P   Q   I   D   K   Y   L   K   S   S   K   Y   I   A    200

601 TGG CCT TTG CAG GGC TGG CAA GCC ACG TTT GGT GGT GGC GAC CAT CCT CCA AAA TCG GAT    660
201 W   P   L   Q   G   W   Q   A   T   F   G   G   G   D   H   P   P   K   S   D    220

661 CTG GTT CCG CCT GGA TCC CCG AAT TCC CGG GTC GAC TCG AGC GGC CGC GCT GAG ATC ACC    720
221 L   V   P   R   G   S   P   N   S   R   V   D   S   S   G   R   A   E   I   T    240

721 AGG ATC CCT CTG TAC AAA GGC AAG TCT CTG AGG AAG GCG CTG AAG GAG CAT GGG CTT CTG    780
241 R   I   P   L   Y   K   G   K   S   L   R   K   A   L   K   E   H   G   L   L    260

781 GAG GAC TTC CTG CAG AAA CAG CAG TAT GGC ATC AGC AGC AAG TAC TCC GGC TTC GTC GTC    840
261 E   D   F   L   Q   K   Q   Q   Y   G   I   S   S   K   Y   S   G   F   V   V    280

841 TAT ACC GAC TGT ACC GAG TCC GGT CAG AAC CTC TGT CTC TGT GAG GGT TCC AAC GTC TGT    900
281 Y   T   D   C   T   E   S   G   Q   N   L   C   L   C   E   G   S   N   V   C    300

901 GGT CAG GGT AAC AAG TGT ATC CTC GGT TCC GAC GGT GAG AAG AAC CAG TGT GTC ACC GGT    960
301 G   Q   G   N   K   C   I   L   G   S   D   G   E   K   N   Q   C   V   T   G    320

961 GAG GGA ACC CCA AAG CCA CAG TCC CAC AAC GAC GGT GAC TTT GAG GAG ATC CCA GAG GAG    1020
321 E   G   T   P   K   P   Q   S   H   N   D   G   D   F   E   E   I   P   E   E    340

1021 TAT CTC CAG TAA agatctaagcttgctgctgctatcgaattcctgcagcccggggatccactagttctagagcgg    1096
341  Y   L   Q   *                                                                     344
```

FIGURE 2

Nucleotide sequence and the deduced amino acid sequence of a His-Pro-cGH fusion.

```
                         Poly Histidine Site
  1 ATG CGG GGT TCT CAT CAT CAT CAT CAT CAT GGT ATG GCT AGC ATG ACT GGT GGA CAG CAA  60
  1  M   R   G   S   H   H   H   H   H   H   G   M   A   S   M   T   G   G   Q   Q   20
                                 EK recognition site
 61 ATG GGT CGG GAT CTG TAC GAC GAT GAC GAT AAG GAT CCG AGC TCG AGA TCT GCA GAA ATC 120
 21  M   G   R   D   L   T   D   D   D   D   K   D   P   S   S   R   S   A   E   I   40
                                              ↑
121 GGA TCC GCT GAG ATC ACC AGG ATC CCT CTG TAC AAA GGC AAG TCT CTG AGG AAG GCG CTG 180
 41  G   S   A   E   I   T   R   I   P   L   Y   K   G   K   S   L   R   K   A   L   60

181 AAG GAG CAT GGG CTT CTG GAG GAC TTC CTG CAG AAA CAG CAG TAT GGC ATC AGC AGC AAG 240
 61  K   E   H   G   L   L   E   D   F   L   Q   K   Q   Q   Y   G   I   S   S   K   80

241 TAC TCC GGC TTC TCA GAC AAC CAG CGG CTC TTC AAT AAT GCA GTC ATT CGT GTA CAA CAC 300
 81  Y   S   G   F   S   D   N   Q   R   L   F   N   N   A   V   I   R   V   Q   H  100
                    ≠
301 CTG CAC CAG CTG GCT GCA AAA ATG ATT AAC GAC TTT GAG GAC AGC CTG TTG CCT GAG GAA 360
101  L   H   Q   L   A   A   K   M   I   N   D   F   E   D   S   L   L   P   E   E  120

361 CGC AGA CAG CTG AGT AAA ATC TTC CCT CTG TCT TTC TGC AAT TCT GAC TAC ATT GAG GCG 420
121  R   R   Q   L   S   K   I   F   P   L   S   F   C   N   S   D   Y   I   E   A  140

421 CCT GCT GGA AAA GAT GAA ACA CAG AAG ACC TCT ATG CTG AAG CTT CTT CGC ATC TCT TTT 480
141  P   A   G   K   D   E   T   Q   K   S   S   M   L   K   L   L   R   I   S   F  160

481 CAC CTC ATT GAG TCC TGG GAG TTC CCA AGC CAG TCC CTG AGC GGA ACC GTC TCA AAC AGC 540
161  H   L   I   E   S   W   E   F   P   S   Q   S   L   S   G   T   V   S   N   S  180

541 CTG ACC GTA GGG AAC CCC AAC CAG CTC ACT GAG AAG CTG GCC GAC TTG AAA ATG GGC ATC 600
181  L   T   V   G   N   P   N   Q   L   T   E   K   L   A   D   L   K   M   G   I  200
  S   D   N   Q   R   L   F   N   N   A   V   I   R   V   Q   H  100
                ↑
301 CTG CAC CAG CTG GCT GCA AAA ATG ATT AAC GAC TTT GAG GAC AGC CTG TTG CCT GAG GAA 360
101  L   H   Q   L   A   A   K   M   I   N   D   F   E   D   S   L   L   P   E   E  120

361 CGC AGA CAG CTG AGT AAA ATC TTC CCT CTG TCT TTC TGC AAT TCT GAC TAC ATT GAG GCG 420
121  R   R   Q   L   S   K   I   F   P   L   S   F   C   N   S   D   Y   I   E   A  140

421 CCT GCT GGA AAA GAT GAA ACA CAG AAG AGC TCT ATG CTG AAG CTT CTT CGC ATC TCT TTT 480
141  P   A   G   K   D   E   T   Q   K   S   S   M   L   K   L   L   R   I   S   F  160

481 CAC CTC ATT GAG TCC TGG GAG TTC CCA AGC CAG TCC CTG AGC GGA ACC GTC TCA AAC AGC 540
161  H   L   I   E   S   W   E   F   P   S   Q   S   L   S   G   T   V   S   N   S  180

541 CTG ACC GTA GGG AAC CCC AAC CAG CTC ACT GAG AAG CTG GCC GAC TTG AAA ATG GGC ATC 600
181  L   T   V   G   N   P   N   Q   L   T   E   K   L   A   D   L   K   M   G   I  200
```

FIGURE 2 (Cont'd)

```
601 AGT GTG CTC ATC CAG GCA TGT CTC GAT GGT CAA CCA AAC ATG GAT GAT AAC GAC TCC TTG 660
201  S   V   L   I   Q   A   C   L   D   G   Q   P   N   M   D   D   N   D   S   L  220

661 CCG CTG CCT TTT GAG GAC TTC TAC TTG ACC ATG GGG GAG AAC AAC CTC AGA GAG AGC TTT 720
221  P   L   P   F   E   D   F   Y   L   T   M   G   E   N   N   L   R   E   S   F  240

721 CGT CTG CTG GCT TGC TTC AAG AAG GAC ATG CAC AAA GTC GAG ACC TAC TTG AGG GTT GCA 780
241  R   L   L   A   C   F   K   K   D   M   H   K   V   E   T   Y   L   R   V   A  260

781 AAT TGC AGG AGA TCC CTG GAT TCC AAC TGC ACC CTG TAG
261  N   C   R   R   S   L   D   S   N   C   T   L   *
```

FIGURE 6

```
AEITRIPLYKGKSLRKALKEHGLLEDFLQKQQYGISSKYSGF   W.t. chymosin
AEITRIPLYKGKSLRKALKEHGLLEDFLQKQQYGISSK---F   KLIP 4
----------KSLRKALKEHGLLEDFLQKQQYGISSK---F    KLIP 11
-----------------KEHGLLEDFLQKQQYGISSK---F    KLIP 12
-------------------------LQKQQYGISSK---F    KLIP 14
----------------------------------GISSK---F KLIP 15
---------------------------------------GR   KLIP 16
```

FIGURE 7

GST-KLIP4-cystatin

```
  1 ATG TCC CCT ATA CTA GGT TAT TGG AAA ATT AAG GGC CTT GTG CAA CCC ACT CGA CTT CTT  60
  1  M   S   P   I   L   G   Y   W   K   I   K   G   L   V   Q   P   T   R   L   L   20

61 TTG GAA TAT CTT GAA GAA AAA TAT GAA GAG CAT TTG TAT GAG CGC GAT GAA GGT GAT AAA 120
 21  L   E   Y   L   E   E   K   Y   E   E   H   L   Y   E   R   D   E   G   D   K   40

121 TGG CGA AAC AAA AAG TTT GAA TTG GGT TTG GAG TTT CCC AAT CTT CCT TAT TAT ATT GAT 180
 41  W   R   N   K   K   F   E   L   G   L   E   F   P   N   L   P   Y   Y   I   D   60

181 GGT GAT GTT AAA TTA ACA CAG TCT ATG GCC ATC ATA CGT TAT ATA GCT GAC AAG CAC AAC 240
 61  G   D   V   K   L   T   Q   S   M   A   I   I   R   Y   I   A   D   K   H   N   80

241 ATG TTG GGT GGT TGT CCA AAA GAG CGT GCA GAG ATT TCA ATG CTT GAA GGA GCG GTT TTG 300
 81  M   L   G   G   C   P   K   E   R   A   E   I   S   M   L   E   G   A   V   L  100

301 GAT ATT AGA TAC GGT GTT TCG AGA ATT GCA TAT AGT AAA GAC TTT GAA ACT CTC AAA GTT 360
101  D   I   R   Y   G   V   S   R   I   A   Y   S   K   D   F   E   T   L   K   V  120

361 GAT TTT CTT AGC AAG CTA CCT GAA ATG CTG AAA ATG TTC GAA GAT CGT TTA TGT CAT AAA 420
121  D   F   L   S   K   L   P   E   M   L   K   M   F   E   D   R   L   C   H   K  140

421 ACA TAT TTA AAT GGT GAT CAT GTA ACC CAT CCT GAC TTC ATG TTG TAT GAC GCT CTT GAT 480
141  T   Y   L   N   G   D   H   V   T   H   P   D   F   M   L   Y   D   A   L   D  160

481 GTT GTT TTA TAC ATG GAC CCA ATG TGC CTG GAT GCG TTC CCA AAA TTA GTT TGT TTT AAA 540
161  V   V   L   Y   M   D   P   M   C   L   D   A   F   P   K   L   V   C   F   K  180

541 AAA CGT ATT GAA GCT ATC CCA CAA ATT GAT AAG TAC TTG AAA TCC AGC AAG TAT ATA GCA 600
181  K   R   I   E   A   I   P   Q   I   D   K   Y   L   K   S   S   K   Y   I   A  200

601 TGG CCT TTG CAG GGC TGG CAA GCC ACG TTT GGT GGT GGC GAC CAT CCT CCA AAA TCG GAT 660
201  W   P   L   Q   G   W   Q   A   T   F   G   G   G   D   H   P   P   K   S   D  220

661 CTG GTT CCG CGT GGA TCC CCG AAT TCC CGG GTC GAC TCG AGC GGC CGC GCT GAG ATC ACC 720
221  L   V   P   R   G   S   P   N   S   R   V   D   S   S   G   R   A   E   I   T  240

721 AGG ATC CCT CTG TAC AAA GGC AAG TCT CTG AGG AAG GCG CTG AAG GAG CAT GGG CTT CTG 780
241  R   I   P   L   Y   K   G   K   S   L   R   K   A   L   K   E   H   G   L   L  260

781 GAG GAC TTC CTG CAG AAA CAG CAG TAT GGC ATC AGC AGC AAG TTC ATG TCG AGC GAC GGA 840
261  E   D   F   L   Q   K   Q   Q   Y   G   I   S   S   K   F   M   S   S   D   G  280

841 GGG CCG GTG CTT GGC GGC GTC GAG CCG GTG GGG AAC GAG AAC GAC CTC CAC CTC GTC GAC 900
281  G   P   V   L   G   G   V   E   P   V   G   N   E   N   D   L   H   L   V   D  300

901 CTC GCC CGC TTC GCC GTC ACC GAG CAC AAC AAG AAG GCC AAT TCT CTG CTG GAG TTC GAG 960
301  L   A   R   F   A   V   T   E   H   N   K   K   A   N   S   L   L   E   F   E  320

961 AAG CTT GTG AGT GTG AAG CAG CAA GTT GTC GCT GGC ACT TTG TAC TAT TTC ACA ATT GAG 1020
321  K   L   V   S   V   K   Q   Q   V   V   A   G   T   L   Y   Y   F   T   I   E  340

1021 GTG AAG GAA GGG GAT GCC AAG AAG CTC TAT GAA GCT AAG GTC TGG GAG AAA CCA TGG ATG 1080
341  V   K   E   G   D   A   K   K   L   Y   E   A   K   V   W   E   K   P   W   M  360

1081 GAC TTC AAG GAG CTC CAG GAG TTC AAG CCT GTC GAT GCC AGT GCA AAT GCC TAA         1033
361  D   F   K   E   L   Q   E   F   K   P   V   D   A   S   A   N   A   -           383
```

FIGURE 8

GST-KLIP11-cystatin

```
   1 ATG TCC CCT ATA CTA GGT TAT TGG AAA ATT AAG GGC CTT GTG CAA CCC ACT CGA CTT CTT   60
   1  M   S   P   I   L   G   Y   W   K   I   K   G   L   V   Q   P   T   R   L   L   20

61 TTG GAA TAT CTT GAA GAA AAA TAT GAA GAG CAT TTG TAT GAG CGC GAT GAA GGT GAT AAA  120
  21  L   E   Y   L   E   E   K   Y   E   E   H   L   Y   E   R   D   E   G   D   K   40

121 TGG CGA AAC AAA AAG TTT GAA TTG GGT TTG GAG TTT CCC AAT CTT CCT TAT TAT ATT GAT  180
  41  W   R   N   K   K   F   E   L   G   L   E   F   P   N   L   P   Y   Y   I   D   60

181 GGT GAT GTT AAA TTA ACA CAG TCT ATG GCC ATC ATA CGT TAT ATA GCT GAC AAG CAC AAC  240
  61  G   D   V   K   L   T   Q   S   M   A   I   I   R   Y   I   A   D   K   H   N   80

241 ATG TTG GGT GGT TGT CCA AAA GAG CGT GCA GAG ATT TCA ATG CTT GAA GGA GCG GTT TTG  300
  81  M   L   G   G   C   P   K   E   R   A   E   I   S   M   L   E   G   A   V   L  100

301 GAT ATT AGA TAC GGT GTT TCG AGA ATT GCA TAT AGT AAA GAC TTT GAA ACT CTC AAA GTT  360
 101  D   I   R   Y   G   V   S   R   I   A   Y   S   K   D   F   E   T   L   K   V  120

361 GAT TTT CTT AGC AAG CTA CCT GAA ATG CTG AAA ATG TTC GAA GAT CGT TTA TGT CAT AAA  420
 121  D   F   L   S   K   L   P   E   M   L   K   M   F   E   D   R   L   C   H   K  140

421 ACA TAT TTA AAT GGT GAT CAT GTA ACC CAT CCT GAC TTC ATG TTG TAT GAC GCT CTT GAT  480
 141  T   Y   L   N   G   D   H   V   T   H   P   D   F   M   L   Y   D   A   L   D  160

481 GTT GTT TTA TAC ATG GAC CCA ATG TGC CTG GAT GCG TTC CCA AAA TTA GTT TGT TTT AAA  540
 161  V   V   L   Y   M   D   P   M   C   L   D   A   F   P   K   L   V   C   F   K  180

541 AAA CGT ATT GAA GCT ATC CCA CAA ATT GAT AAG TAC TTG AAA TCC AGC AAG TAT ATA GCA  600
 181  K   R   I   E   A   I   P   Q   I   D   K   Y   L   K   S   S   K   Y   I   A  200

601 TGG CCT TTG CAG GGC TGG CAA GCC ACG TTT GGT GGT GGC GAC CAT CCT CCA AAA TCG GAT  660
 201  W   P   L   Q   G   W   Q   A   T   F   G   G   G   D   H   P   P   K   S   D  220

661 CTG GTT CCG CGT GGA TCC CCG AAT TCC CGG GTC GAC TCG AGC GGC CGC AAG TCT CTG AGG  720
 221  L   V   P   R   G   S   P   N   S   R   V   D   S   S   G   R   K̲   S̲   L̲   R̲  240

721 AAG GCG CTG AAG GAG CAT GGG CTT CTG GAG GAC TTC CTG CAG AAA CAG CAG TAT GGC ATC  780
 241  K̲   A̲   L̲   K̲   E̲   H̲   G̲   L̲   L̲   E̲   D̲   F̲   L̲   Q̲   K̲   Q̲   Q̲   Y̲   G̲   I̲  260

781 AGC AGC AAG TTC ATG TCG AGC GAC GGA GGG CCG GTG CTT GGC GGC GTC GAG CCG GTG GGG  840
 261  S̲   S̲   K̲   F̲   M   S   S   D   G   G   P   V   L   G   G   V   E   P   V   G  280

841 AAC GAG AAC GAC CTC CAC CTC GTC GAC CTC GCC CGC TTC GCC GTC ACC GAG CAC AAC AAG  900
 281  N   E   N   D   L   H   L   V   D   L   A   R   F   A   V   T   E   H   N   K  300

901 AAG GCC AAT TCT CTG CTG GAG TTC GAG AAG CTT GTG AGT GTG AAG CAG CAA GTT GTC GCT  960
 301  K   A   N   S   L   L   E   F   E   K   L   V   S   V   K   Q   Q   V   V   A  320

961 GGC ACT TTG TAC TAT TTC ACA ATT GAG GTG AAG GAA GGG GAT GCC AAG AAG CTC TAT GAA 1020
 321  G   T   L   Y   Y   F   T   I   E   V   K   E   G   D   A   K   K   L   Y   E  340

1021 GCT AAG GTC TGG GAG AAA CCA TGG ATG GAC TTC AAG GAG CTC CAG GAG TTC AAG CCT GTC 1080
 341  A   K   V   W   E   K   P   W   M   D   F   K   E   L   Q   E   F   K   P   V  360

1081 GAT GCC AGT GCA AAT GCC TAA                                                      1102
 361  D   A   S   A   N   A   -                                                       366
```

FIGURE 9

GST-KLIP12-cystatin

```
  1 ATG TCC CCT ATA CTA GGT TAT TGG AAA ATT AAG GGC CTT GTG CAA CCC ACT CGA CTT CTT  60
  1  M   S   P   I   L   G   Y   W   K   I   K   G   L   V   Q   P   T   R   L   L   20

61 TTG GAA TAT CTT GAA GAA AAA TAT GAA GAG CAT TTG TAT GAG CGC GAT GAA GGT GAT AAA 120
 21  L   E   Y   L   E   E   K   Y   E   E   H   L   Y   E   R   D   E   G   D   K   40

121 TGG CGA AAC AAA AAG TTT GAA TTG GGT TTG GAG TTT CCC AAT CTT CCT TAT TAT ATT GAT 180
 41  W   R   N   K   K   F   E   L   G   L   E   F   P   N   L   P   Y   Y   I   D   60

181 GGT GAT GTT AAA TTA ACA CAG TCT ATG GCC ATC ATA CGT TAT ATA GCT GAC AAG CAC AAC 240
 61  G   D   V   K   L   T   Q   S   M   A   I   I   R   Y   I   A   D   K   H   N   80

241 ATG TTG GGT GGT TGT CCA AAA GAG CGT GCA GAG ATT TCA ATG CTT GAA GGA GCG GTT TTG 300
 81  M   L   G   G   C   P   K   E   R   A   E   I   S   M   L   E   G   A   V   L  100

301 GAT ATT AGA TAC GGT GTT TCG AGA ATT GCA TAT AGT AAA GAC TTT GAA ACT CTC AAA GTT 360
101  D   I   R   Y   G   V   S   R   I   A   Y   S   K   D   F   E   T   L   K   V  120

361 GAT TTT CTT AGC AAG CTA CCT GAA ATG CTG AAA ATG TTC GAA GAT CGT TTA TGT CAT AAA 420
121  D   F   L   S   K   L   P   E   M   L   K   M   F   E   D   R   L   C   H   K  140

421 ACA TAT TTA AAT GGT GAT CAT GTA ACC CAT CCT GAC TTC ATG TTG TAT GAC GCT CTT GAT 480
141  T   Y   L   N   G   D   H   V   T   H   P   D   F   M   L   Y   D   A   L   D  160

481 GTT GTT TTA TAC ATG GAC CCA ATG TGC CTG GAT GCG TTC CCA AAA TTA GTT TGT TTT AAA 540
161  V   V   L   Y   M   D   P   M   C   L   D   A   F   P   K   L   V   C   F   K  180

541 AAA CGT ATT GAA GCT ATC CCA CAA ATT GAT AAG TAC TTG AAA TCC AGC AAG TAT ATA GCA 600
181  K   R   I   E   A   I   P   Q   I   D   K   Y   L   K   S   S   K   Y   I   A  200

601 TGG CCT TTG CAG GGC TGG CAA GCC ACG TTT GGT GGT GGC GAC CAT CCT CCA AAA TCG GAT 660
201  W   P   L   Q   G   W   Q   A   T   F   G   G   G   D   H   P   P   K   S   D  220

661 CTG GTT CCG CGT GGA TCC CCG AAT TCC CGG GTC GAC TCG AGC GGC CGC AAG GAG CAT GGG 720
221  L   V   P   R   G   S   P   N   S   R   V   D   S   S   G   R   K   E   H   G  240

721 CTT CTG GAG GAC TTC CTG CAG AAA CAG CAG TAT GGC ATC AGC AGC AAG TTC ATG TCG AGC 780
241  L   L   E   D   F   L   Q   K   Q   Q   Y   G   I   S   S   K   F   M   S   S  260

781 GAC GGA GGG CCG GTG CTT GGC GGC GTC GAG CCG GTG GGG AAC GAG AAC GAC CTC CAC CTC 840
261  D   G   G   P   V   L   G   G   V   E   P   V   G   N   E   N   D   L   H   L  280

841 GTC GAC CTC GCC CGC TTC GCC GTC ACC GAG CAC AAC AAG AAG GCC AAT TCT CTG CTG GAG 900
281  V   D   L   A   R   F   A   V   T   E   H   N   K   K   A   N   S   L   L   E  300

901 TTC GAG AAG CTT GTG AGT GTG AAG CAG CAA GTT GTC GCT GGC ACT TTG TAC TAT TTC ACA 960
301  F   E   K   L   V   S   V   K   Q   Q   V   V   A   G   T   L   Y   Y   F   T  320

961 ATT GAG GTG AAG GAA GGG GAT GCC AAG AAG CTC TAT GAA GCT AAG GTC TGG GAG AAA CCA 1020
321  I   E   V   K   E   G   D   A   K   K   L   Y   E   A   K   V   W   E   K   P  340

1021 TGG ATG GAC TTC AAG GAG CTC CAG GAG TTC AAG CCT GTC GAT GCC AGT GCA AAT GCC TAA 1080
341  W   M   D   F   K   E   L   Q   E   F   K   P   V   D   A   S   A   N   A   -  359
```

FIGURE 10

GST-KLIP14-cystatin

```
   1 ATG TCC CCT ATA CTA GGT TAT TGG AAA ATT AAG GGC CTT GTG CAA CCC ACT CGA CTT CTT   60
   1  M   S   P   I   L   G   Y   W   K   I   K   G   L   V   Q   P   T   R   L   L   20

61 TTG GAA TAT CTT GAA GAA AAA TAT GAA GAG CAT TTG TAT GAG CGC GAT GAA GGT GAT AAA  120
  21  L   E   Y   L   E   E   K   Y   E   E   H   L   Y   E   R   D   E   G   D   K   40

121 TGG CGA AAC AAA AAG TTT GAA TTG GGT TTG GAG TTT CCC AAT CTT CCT TAT TAT ATT GAT  180
  41  W   R   N   K   K   F   E   L   G   L   E   F   P   N   L   P   Y   Y   I   D   60

181 GGT GAT GTT AAA TTA ACA CAG TCT ATG GCC ATC ATA CGT TAT ATA GCT GAC AAG CAC AAC  240
  61  G   D   V   K   L   T   Q   S   M   A   I   I   R   Y   I   A   D   K   H   N   80

241 ATG TTG GGT GGT TGT CCA AAA GAG CGT GCA GAG ATT TCA ATG CTT GAA GGA GCG GTT TTG  300
  81  M   L   G   G   C   P   K   E   R   A   E   I   S   M   L   E   G   A   V   L  100

301 GAT ATT AGA TAC GGT GTT TCG AGA ATT GCA TAT AGT AAA GAC TTT GAA ACT CTC AAA GTT  360
 101  D   I   R   Y   G   V   S   R   I   A   Y   S   K   D   F   E   T   L   K   V  120

361 GAT TTT CTT AGC AAG CTA CCT GAA ATG CTG AAA ATG TTC GAA GAT CGT TTA TGT CAT AAA  420
 121  D   F   L   S   K   L   P   E   M   L   K   M   F   E   D   R   L   C   H   K  140

421 ACA TAT TTA AAT GGT GAT CAT GTA ACC CAT CCT GAC TTC ATG TTG TAT GAC GCT CTT GAT  480
 141  T   Y   L   N   G   D   H   V   T   H   P   D   F   M   L   Y   D   A   L   D  160

481 GTT GTT TTA TAC ATG GAC CCA ATG TGC CTG GAT GCG TTC CCA AAA TTA GTT TGT TTT AAA  540
 161  V   V   L   Y   M   D   P   M   C   L   D   A   F   P   K   L   V   C   F   K  180

541 AAA CGT ATT GAA GCT ATC CCA CAA ATT GAT AAG TAC TTG AAA TCC AGC AAG TAT ATA GCA  600
 181  K   R   I   E   A   I   P   Q   I   D   K   Y   L   K   S   S   K   Y   I   A  200

601 TGG CCT TTG CAG GGC TGG CAA GCC ACG TTT GGT GGT GGC GAC CAT CCT CCA AAA TCG GAT  660
 201  W   P   L   Q   G   W   Q   A   T   F   G   G   G   D   H   P   P   K   S   D  220

661 CTG GTT CCG CGT GGA TCC CCG AAT TCC CGG GTC GAC TCG AGC GGC CGC CTG CAG AAA CAG  720
 221  L   V   P   R   G   S   P   N   S   R   V   D   S   S   G   R   L   Q   K   Q  240

720 CAG TAT GGC ATC AGC AGC AAG TTC ATG TCG AGC GAC GGA GGG CCG GTG CTT GGC GGC GTC  780
 241  Q   Y   G   I   S   S   K   F   M   S   S   D   G   G   P   V   L   G   G   V  260

781 GAG CCG GTG GGG AAC GAG AAC GAC CTC CAC CTC GTC GAC CTC GCC CGC TTC GCC GTC ACC  840
 841  E   P   V   G   N   E   N   D   L   H   L   V   D   L   A   R   F   A   V   T  280

841 GAG CAC AAC AAG AAG GCC AAT TCT CTG CTG GAG TTC GAG AAG CTT GTG AGT GTG AAG CAG  900
 281  E   H   N   K   K   A   N   S   L   L   E   F   E   K   L   V   S   V   K   Q  300

901 CAA GTT GTC GCT GGC ACT TTG TAC TAT TTC ACA ATT GAG GTG AAG GAA GGG GAT GCC AAG  960
 301  Q   V   V   A   G   T   L   Y   Y   F   T   I   E   V   K   E   G   D   A   K  320

961 AAG CTC TAT GAA GCT AAG GTC TGG GAG AAA CCA TGG ATG GAC TTC AAG GAG CTC CAG GAG 1020
 321  K   L   Y   E   A   K   V   W   E   K   P   W   M   D   F   K   E   L   Q   E  340

1021 TTC AAG CCT GTC GAT GCC AGT GCA AAT GCC TAA                                     1053
 341  F   K   P   V   D   A   S   A   N   A   -                                      350
```

FIGURE 11

GST-KLIP15-cystatin

```
   1  ATG TCC CCT ATA CTA GGT TAT TGG AAA ATT AAG GGC CTT GTG CAA CCC ACT CGA CTT CTT   60
   1   M   S   P   I   L   G   Y   W   K   I   K   G   L   V   Q   P   T   R   L   L   20

61  TTG GAA TAT CTT GAA GAA AAA TAT GAA GAG CAT TTG TAT GAG CGC GAT GAA GGT GAT AAA  120
  21   L   E   Y   L   E   E   K   Y   E   E   H   L   Y   E   R   D   E   G   D   K   40

121  TGG CGA AAC AAA AAG TTT GAA TTG GGT TTG GAG TTT CCC AAT CTT CCT TAT TAT ATT GAT  180
  41   W   R   N   K   K   F   E   L   G   L   E   F   P   N   L   P   Y   Y   I   D   60

181  GGT GAT GTT AAA TTA ACA CAG TCT ATG GCC ATC ATA CGT TAT ATA GCT GAC AAG CAC AAC  240
  61   G   D   V   K   L   T   Q   S   M   A   I   I   R   Y   I   A   D   K   H   N   80

241  ATG TTG GGT GGT TGT CCA AAA GAG CGT GCA GAG ATT TCA ATG CTT GAA GGA GCG GTT TTG  300
  81   M   L   G   G   C   P   K   E   R   A   E   I   S   M   L   E   G   A   V   L  100

301  GAT ATT AGA TAC GGT GTT TCG AGA ATT GCA TAT AGT AAA GAC TTT GAA ACT CTC AAA GTT  360
 101   D   I   R   Y   G   V   S   R   I   A   Y   S   K   D   F   E   T   L   K   V  120

361  GAT TTT CTT AGC AAG CTA CCT GAA ATG CTG AAA ATG TTC GAA GAT CGT TTA TGT CAT AAA  420
 121   D   F   L   S   K   L   P   E   M   L   K   M   F   E   D   R   L   C   H   K  140

421  ACA TAT TTA AAT GGT GAT CAT GTA ACC CAT CCT GAC TTC ATG TTG TAT GAC GCT CTT GAT  480
 141   T   Y   L   N   G   D   H   V   T   H   P   D   F   M   L   Y   D   A   L   D  160

481  GTT GTT TTA TAC ATG GAC CCA ATG TGC CTG GAT GCG TTC CCA AAA TTA GTT TGT TTT AAA  540
 161   V   V   L   Y   M   D   P   M   C   L   D   A   F   P   K   L   V   C   F   K  180

541  AAA CGT ATT GAA GCT ATC CCA CAA ATT GAT AAG TAC TTG AAA TCC AGC AAG TAT ATA GCA  600
 181   K   R   I   E   A   I   P   Q   I   D   K   Y   L   K   S   S   K   Y   I   A  200

601  TGG CCT TTG CAG GGC TGG CAA GCC ACG TTT GGT GGT GGC GAC CAT CCT CCA AAA TCG GAT  660
 201   W   P   L   Q   G   W   Q   A   T   F   G   G   G   D   H   P   P   K   S   D  220

661  CTG GTT CCG CGT GGA TCC CCG AAT TCC CGG GTC GAC TCG AGC GGC CGC GGC ATC AGC AGC  720
 221   L   V   P   R   G   S   P   N   S   R   V   D   S   S   G   R   G   I   S   S  240

721  AAG TTC ATG TCG AGC GAC GGA GGG CCG GTG CTT GGC GGC GTC GAG CCG GTG GGG AAC GAG  780
 241   K   F   M   S   S   D   G   G   P   V   L   G   G   V   E   P   V   G   N   E  260

781  AAC GAC CTC CAC CTC GTC GAC CTC GCC CGC TTC GCC GTC ACC GAG CAC AAC AAG AAG GCC  840
 261   N   D   L   H   L   V   D   L   A   R   F   A   V   T   E   H   N   K   K   A  280

841  AAT TCT CTG CTG GAG TTC GAG AAG CTT GTG AGT GTG AAG CAG CAA GTT GTC GCT GGC ACT  900
 281   N   S   L   L   E   F   E   K   L   V   S   V   K   Q   Q   V   V   A   G   T  300

901  TTG TAC TAT TTC ACA ATT GAG GTG AAG GAA GGG GAT GCC AAG AAG CTC TAT GAA GCT AAG  960
 301   L   Y   Y   F   T   I   E   V   K   E   G   D   A   K   K   L   Y   E   A   K  320

961  GTC TGG GAG AAA CCA TGG ATG GAC TTC AAG GAG CTC CAG GAG TTC AAG CCT GTC GAT GCC 1020
 321   V   W   E   K   P   W   M   D   F   K   E   L   Q   E   F   K   P   V   D   A  340

1021  AGT GCA AAT GCC TAA                                                              1035
 341   S   A   N   A   -                                                                344
```

FIGURE 12

GST-KLIP16-cystatin

```
  1 ATG TCC CCT ATA CTA GGT TAT TGG AAA ATT AAG GGC CTT GTG CAA CCC ACT CGA CTT CTT   60
  1  M   S   P   I   L   G   Y   W   K   I   K   G   L   V   Q   P   T   R   L   L    20

61 TTG GAA TAT CTT GAA GAA AAA TAT GAA GAG CAT TTG TAT GAG CGC GAT GAA GGT GAT AAA  120
 21  L   E   Y   L   E   E   K   Y   E   E   H   L   Y   E   R   D   E   G   D   K    40

121 TGG CGA AAC AAA AAG TTT GAA TTG GGT TTG GAG TTT CCC AAT CTT CCT TAT TAT ATT GAT  180
 41  W   R   N   K   K   F   E   L   G   L   E   F   P   N   L   P   Y   Y   I   D    60

181 GGT GAT GTT AAA TTA ACA CAG TCT ATG GCC ATC ATA CGT TAT ATA GCT GAC AAG CAC AAC  240
 61  G   D   V   K   L   T   Q   S   M   A   I   I   R   Y   I   A   D   K   H   N    80

241 ATG TTG GGT GGT TGT CCA AAA GAG CGT GCA GAG ATT TCA ATG CTT GAA GGA GCG GTT TTG  300
 81  M   L   G   G   C   P   K   E   R   A   E   I   S   M   L   E   G   A   V   L   100

301 GAT ATT AGA TAC GGT GTT TCG AGA ATT GCA TAT AGT AAA GAC TTT GAA ACT CTC AAA GTT  360
101  D   I   R   Y   G   V   S   R   I   A   Y   S   K   D   F   E   T   L   K   V   120

361 GAT TTT CTT AGC AAG CTA CCT GAA ATG CTG AAA ATG TTC GAA GAT CGT TTA TGT CAT AAA  420
121  D   F   L   S   K   L   P   E   M   L   K   M   F   E   D   R   L   C   H   K   140

421 ACA TAT TTA AAT GGT GAT CAT GTA ACC CAT CCT GAC TTC ATG TTG TAT GAC GCT CTT GAT  480
141  T   Y   L   N   G   D   H   V   T   H   P   D   F   M   L   Y   D   A   L   D   160

481 GTT GTT TTA TAC ATG GAC CCA ATG TGC CTG GAT GCG TTC CCA AAA TTA GTT TGT TTT AAA  540
161  V   V   L   Y   M   D   P   M   C   L   D   A   F   P   K   L   V   C   F   K   180

541 AAA CGT ATT GAA GCT ATC CCA CAA ATT GAT AAG TAC TTG AAA TCC AGC AAG TAT ATA GCA  600
181  K   R   I   E   A   I   P   Q   I   D   K   Y   L   K   S   S   K   Y   I   A   200

601 TGG CCT TTG CAG GGC TGG CAA GCC ACG TTT GGT GGT GGC GAC CAT CCT CCA AAA TCG GAT  660
201  W   P   L   Q   G   W   Q   A   T   F   G   G   G   D   H   P   P   K   S   D   220

661 CTG GTT CCG CGT GGA TCC CCG AAT TCC CGG GTC GAC TCC AGC GGC CGC ATG TCG AGC GAC  720
221  L   V   P   R   G   S   P   N   S   R   V   D   S   S   G   R   M   S   S   D   240

780 GGA GGG CCG GTG CTT GGC GGC GTC GAG CCG GTG GGG AAC GAG AAC GAC CTC CAC CTC GTC  780
241  G   G   P   V   L   G   G   V   E   P   V   G   N   E   N   D   L   H   L   V   260

781 GAC CTC GCC CGC TTC GCC GTC ACC GAG CAC AAC AAG AAG GCC AAT TCT CTG CTG GAG TTC  840
261  D   L   A   R   F   A   V   T   E   H   N   K   K   A   N   S   L   L   E   F   280

841 GAG AAG CTT GTG AGT GTG AAG CAG CAA GTT GTC GCT GGC ACT TTG TAC TAT TTC ACA ATT  900
281  E   K   L   V   S   V   K   Q   Q   V   V   A   G   T   L   Y   Y   F   T   I   300

901 GAG GTG AAG GAA GGG GAT GCC AAG AAG CTC TAT GAA GCT AAG GTC TGG GAG AAA CCA TGG  960
301  E   V   K   E   G   D   A   K   K   L   Y   E   A   K   V   W   E   K   P   W   320

961 ATG GAC TTC AAG GAG CTC CAG GAG TTC AAG CCT GTC GAT GCC AGT GCA AAT GCC TAA    1017
321  M   D   F   K   E   L   Q   E   F   K   P   V   D   A   S   A   N   A   -       338
```

KLIP4

KLIP 12

KLIP 14

KLIP 15

KLIP 16

METHOD FOR CLEAVAGE OF FUSION PROTEINS

This application is a continuation-in-part of U.S. patent application Ser. No. 09/402,488 filed Feb. 16, 2000, which is a national phase entry application of international patent application serial No. PCT/CA98/00398 filed Apr. 23, 1998, which claims priority from U.S. provisional patent application Ser. No. 60/044,254 filed Apr. 25, 1997 (now abandoned), all of which are incorporated herein by reference.

FIELD OF THE INVENTION

The present invention relates to an improved method for recovering recombinantly produced polypeptides. The method involves expressing the recombinant polypeptide as a fusion protein with a pro-peptide. The pro-peptide-polypeptide fusion protein can be cleaved and the recombinant protein released under the appropriate conditions.

BACKGROUND OF THE INVENTION

The preparation of valuable recombinant (genetically engineered) polypeptides, for example pharmaceutical proteins, relies frequently on techniques which involve the production of these polypeptides as fusion or hybrid proteins. These techniques are based upon the preparation of hybrid genes, i.e. genes comprising genetic material encoding the polypeptide of interest linked to genetic material additional to the gene of interest. Production of the fusion polypeptide involves the introduction of the hybrid gene into a biological host cell system, for example yeast cells, which permits the expression and accumulation of the fusion polypeptide. Recovery of the polypeptide of interest involves the performance of a cleavage reaction which results in the separation of the desired polypeptide from the "fusion partner".

Despite the additional steps which are required to produce a protein of interest as a fusion protein, rather than directly in its active form, the production of hybrid proteins has been found to overcome a number of problems. Firstly, overproduced polypeptides can aggregate in the host cell in insoluble fractions known as inclusion bodies. Conversion of this insoluble material involves often slow and complex refolding methods, making protein purification difficult. Secondly, those proteins which are present in soluble form in the cytoplasm often are subject to degradation by host specific enzymes, thus reducing the amounts of active protein that can be recovered. Linking the polypeptide of interest to a fusion partner has been found to limit these problems. Fusion partners known to the prior art include maltose binding protein (Di Guan et al. (1988) Gene 67: 21-30), glutathione-S-transferase (Johnson (1989) Nature 338: 585-587), ubiquitin (Miller et al. (1989) Biotechnology 7: 698-704), β-galactosidase (Goeddel et al. (1979) Proc. Natl. Acad. Sci. (USA) 76: 106-110), and thioredoxin (LaVallie et al. (1993) Biotechnology 11:187-193).

It has also been proposed to employ fusion partners as affinity peptides. This methodology facilitates the isolation and recovery of the fusion peptide from the host cells by exploiting the physico-chemical properties of the fusion partner. (See, for example, WO 91/11454).

Finally, the use of a fusion partner may enable the production of a peptide which would otherwise be too small to accumulate and recover efficiently from a recombinant host cell system. This technology is described, for example, by Schultz et al., (1987, J. Bacteriol. 169: 5385-5392)

All of these procedures result in the production a hybrid protein in which the protein of interest is linked to an additional polypeptide. In order to recover the active polypeptide it is, in general, necessary to separate the fusion partner from the polypeptide of interest. Most commonly, a cleavage reaction, either by enzymatic or by chemical means, is performed. Such reactions employ agents that act by hydrolysis of peptide bonds and the specificity of the cleavage agent is determined by the identity of the amino acid residue at or near the peptide bond which is cleaved.

Enzymes known to the prior art as "proteolytic enzymes" have been found to be particularly well suited for the cleavage of fusion proteins. The cleavage reaction is performed by contacting the fusion protein with a proteolytic enzyme under appropriate conditions. An example of this methodology is described in U.S. Pat. No. 4,743,679 which discloses a process for the production of human epidermal growth factor comprising cleavage of a fusion protein by *Staphylococcus aureus* V8 protease.

By contrast, chemical cleavage involves the use of chemical agents which are known to permit hydrolysis of peptide bonds under specific conditions. Cyanogenbromide, for example, is known to cleave the polypeptide chain at a methionine residue. A hydrolysis reaction for the cyanogenbromide cleavage of the proteins urease and phosphorylase b based on this technique is described by Sekita et al. ((1975), Keio J. Med. 24: 203-210).

Both chemical and enzymatic cleavage reactions require the presence of a peptide bond which can be cleaved by the cleavage agent which is employed. For this reason it is often desirable to place an appropriate target sequence at the junction of the fusion partner and the target protein. Fusion peptides comprising "linker" sequences containing a target for a proteolytic enzyme may readily be constructed using conventional art-recognized genetic engineering techniques.

Despite their great utility, the prior art cleavage methods have been recognized to be either inefficient or lack cleavage specificity. Inefficient cleavage results in low protein purification efficiency, while the lack of cleavage specificity results in cleavage at several locations resulting in product loss and generation of contaminating fragments. This results frequently in the recovery of only a small fraction of the desired protein. In addition, the currently widely used proteolytic enzymes, such as blood clotting factor Xa and thrombin, are expensive, and contamination of final product with blood pathogens is a consideration.

In view of these shortcomings, the limitations of the cleavage methods known to the prior art are apparent.

Zymogens, such as pepsin and chymosin, are enzymes which are synthesized as inactive precursors in vivo. Under appropriate conditions, zymogens are activated to form the mature active protein in a process involving the cleavage of an amino-terminal peptide which can be referred to as the "pro-peptide", "pro-region" or "pro-sequence". Activation of zymogens may require the presence of an additional specific proteolytic enzyme, for example various hormones, such as insulin, are processed by a specific proteolytic enzyme. Alternatively, activation may occur without an additional enzymatic catalyst. These kinds of zymogens are frequently referred to as "autocatalytically maturing" zymogens. Examples of autocatalytically maturing zymogens include pepsin, pepsinogen and chymosin which are activated by an acidic environment, for example in the mammalian stomach.

The autocatalytic activation and processing of zymogens has been documented extensively (see for example, McCaman and Cummings, (1986), J. Biol. Chem. 261: 15345-15348; Koelsch et al. (1994). FEBS Letters 343: 6-10). It has also been documented that activation of the zymogen does not necessarily require a physical linkage of the pro-peptide to the mature protein (Silen et al. (1989), Nature, 341: 462-464).

There is a need for an improved process for recovering recombinantly produced polypeptides from their expression systems.

SUMMARY OF THE INVENTION

The present inventors have developed a novel method for recovering recombinantly produced polypeptides. The method involves expressing the polypeptide as a fusion protein with a pro-peptide so that the recombinant polypeptide can be cleaved from the pro-peptide under the appropriate conditions.

In one aspect, the invention provides a chimeric nucleic acid sequence encoding a fusion protein, the chimeric nucleic acid sequence comprising a first nucleic acid sequence encoding a pro-peptide derived from an autocatalytically maturing zymogen and a second nucleic acid sequence encoding a polypeptide that is heterologous to the pro-peptide.

In another aspect the present invention provides a fusion protein comprising (a) a pro-peptide derived from an autocatalytically maturing zymogen and (b) a polypeptide that is heterologous to the pro-peptide. In one embodiment, the heterologous polypeptide is a therapeutic or nutritional peptide and the fusion protein may be administered as a pharmaceutical or food composition. In such an embodiment the heterologous polypeptide may be cleaved once the composition is delivered to the host as a result of the physiological conditions at the target organ, tissue or in the bodily fluid.

In a further aspect, the present invention provides a method for the preparation of a recombinant polypeptide comprising
(a) introducing into a host cell an expression vector comprising:
  (1) a nucleic acid sequence capable of regulating transcription in a host cell, operatively linked to
  (2) a chimeric nucleic acid sequence encoding a fusion protein, the chimeric nucleic acid sequence comprising (a) a nucleic acid sequence encoding a pro-peptide derived from an autocatalytically maturing zymogen, linked in reading frame to (b) a nucleic acid sequence heterologous to the pro-peptide and encoding the recombinant polypeptide; operatively linked to
  (3) a nucleic acid sequence encoding a termination region functional in the host cell,
(b) growing the host cell to produce said fusion protein; and
(c) altering the environment of the fusion protein so that the pro-peptide is cleaved from the fusion protein to release the recombinant polypeptide.

The environment of the fusion protein can be altered using many means including altering the pH, temperature or salt concentration or other alterations that permit to pro-peptide to self-cleave from the fusion protein to release to recombinant polypeptide. In a preferred embodiment, the mature zymogen is added to the method in step (c) to assist in the cleavage of the propeptide from the fusion protein.

Other features and advantages of the present invention will become readily apparent from the following detailed description. It should be understood, however, that the detailed description and the specific examples while indicating preferred embodiments of the invention are given by way of illustration only, since various changes and modifications within the spirit and scope of the invention will become apparent to those skilled in the art of this detailed description.

BRIEF DESCRIPTION OF THE DRAWINGS

The invention will now be described in relation to the drawings in which:

FIG. 1 is the nucleic acid (SEQ.ID.NO.:1) and deduced amino acid sequence (SEQ.ID.NO.:2) of a GST-Chymosin pro-peptide-Hirudin sequence.

FIG. 2 is the nucleic acid (SEQ.ID.NO.:3) and deduced amino acid sequence (SEQ.ID.NO.:4) of a poly histidine tagged chymosin pro-peptide carp growth hormone (His-Pro-cGH) fusion protein.

FIG. 6 is an amino acid comparison between wild-type calf chymosin pro-peptide (SEQ.ID.NO.:5), KLIP 4 (SEQ.ID.NO.:6), KLIP 11 (SEQ.ID.NO.:7), KLIP 12 (SEQ.ID.NO.:8), KLIP 14 (SEQ.ID.NO.:9), KLIP 15 (SEQ.ID.NO.: 10), and KLIP 16 (SEQ.ID.NO.:11)

FIG. 7 is the nucleic acid (SEQ.ID.NO.:12) and deduced amino acid sequence (SEQ.ID.NO.:13) of a glutathione S transferase KLIP 4 chymosin pro-peptide cystatin (GST-KLIP4-cystatin) fusion protein.

FIG. 8 is the nucleic acid (SEQ.ID.NO.:14) and deduced amino acid sequence (SEQ.ID.NO.:15) of a glutathione S transferase KLIP 11 chymosin pro-peptide cystatin (GST-KLIP11-cystatin) fusion protein.

FIG. 9 is the nucleic acid (SEQ.ID.NO.:16) and deduced amino acid sequence (SEQ.ID.NO.:17) of a glutathione S transferase KLIP 12 chymosin pro-peptide cystatin (GST-KLIP12-cystatin) fusion protein.

FIG. 10 is the nucleic acid (SEQ.ID.NO.:18) and deduced amino acid sequence (SEQ.ID.NO.:19) of a glutathione S transferase KLIP 14 chymosin pro-peptide cystatin (GST-KLIP14-cystatin) fusion protein.

FIG. 11 is the nucleic acid (SEQ.ID.NO.:20) and deduced amino acid sequence (SEQ.ID.NO.:21) of a glutathione S transferase KLIP 15 chymosin pro-peptide cystatin (GST-KLIP15-cystatin) fusion protein.

FIG. 12 is the nucleic acid (SEQ.ID.NO.:22) and deduced amino acid sequence (SEQ.ID.NO.:23) of a glutathione S transferase KLIP 16 chymosin pro-peptide cystatin (GST-KLIP16-cystatin) fusion protein.

DETAILED DESCRIPTION OF THE INVENTION

Figure 3:
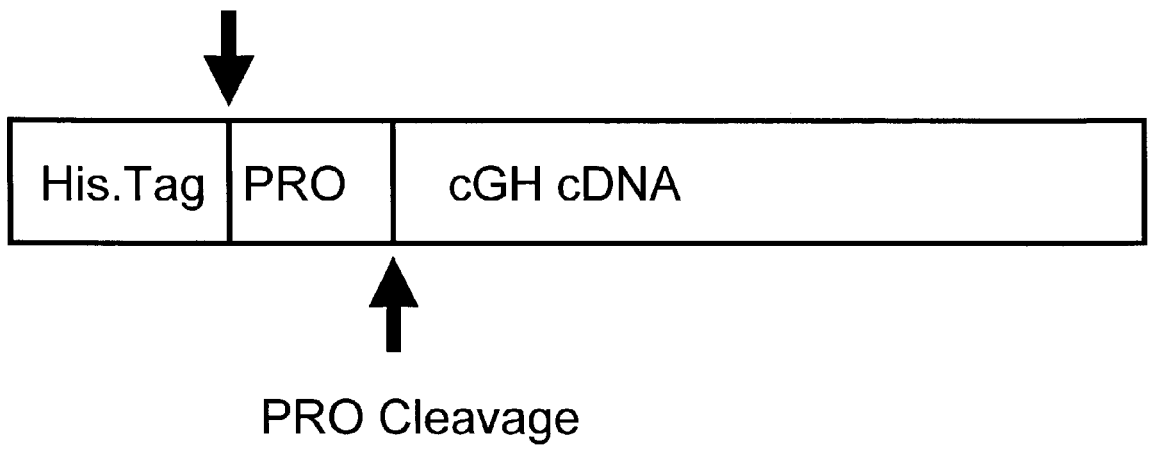
FIG. 3 is a schematic diagram of the Pro-cGH fusion construct.

As hereinbefore mentioned, the present invention relates to a novel method for preparing and recovering recombinant polypeptides, chimeric nucleic acid sequences encoding fusion proteins and fusion proteins useful in pharmaceutical and nutritional compositions.

Accordingly, the present invention provides a method for the preparation of a recombinant polypeptide comprising:
(a) introducing into a host cell an expression vector comprising:
  (1) a nucleic acid sequence capable of regulating transcription in a host cell, operatively linked to
  (2) a chimeric nucleic acid sequence encoding a fusion protein, the chimeric nucleic acid sequence comprising
    (a) a nucleic acid sequence encoding a pro-peptide derived from an autocatalytically maturing zymogen, linked in reading frame to (b) a nucleic acid sequence heterologous to the pro-peptide and encoding the recombinant polypeptide, operatively linked to
  (3) a nucleic acid sequence encoding a termination region functional in said host cell,
b) growing the host cell to produce said fusion protein; and
c) altering the environment of the fusion protein so that the pro-peptide is cleaved from the fusion protein to release the recombinant polypeptide.

The environment of the fusion protein can be altered using many means including altering the pH, temperature or salt concentration or other alterations that permit to pro-peptide to self-cleave from the fusion protein to release to recombinant polypeptide. In a preferred embodiment, the mature zymogen is added to the method in step (c) to assist in the cleavage of the propeptide from the fusion protein The term "pro-peptide" as used herein means the amino terminal portion of a zymogen or a functional portion thereof up to the maturation site.

The term "autocatalytically maturing zymogen" as used herein means that: (i) the zymogen can be processed to its active form without requiring an additional specific protease and that (ii) the mature form of the zymogen can assist in the cleavage reaction.

The term "mature zymogen" as used herein means a zymogen that does not contain the pro-peptide sequence or portion.

The polypeptide can be any polypeptide that is heterologous to the pro-peptide, meaning that it is not the mature protein that is normally associated with the pro-peptide as a zymogen.

In another aspect, the invention provides a chimeric nucleic acid sequence encoding a fusion protein, the chimeric nucleic acid sequence comprising a first nucleic acid sequence encoding a pro-peptide derived from an autocatalytically maturing zymogen and a second nucleic acid sequence encoding a polypeptide that is heterologous to the pro-peptide. The chimeric nucleic acid sequence generally does not include a nucleic acid sequence encoding the entire zymogen.

The chimeric nucleic acid sequences which encode the fusion proteins of the present invention can be incorporated in a known manner into a recombinant-expression vector which ensures good expression in a host cell.

Accordingly, the present invention also includes a recombinant expression vector comprising a chimeric nucleic acid molecule of the present invention operatively linked to a regulatory sequence and termination region suitable for expression in a host cell.

The term "nucleic acid sequence" refers to a sequence of nucleotide or nucleoside monomers consisting of naturally occurring bases, sugars, and intersugar (backbone) linkages. The term also includes modified or substituted sequences comprising non-naturally occurring monomers or portions thereof, which function similarly. The nucleic acid sequences of the present invention may be ribonucleic (RNA) or deoxyribonucleic acids (DNA) and may contain naturally occurring bases including adenine, guanine, cytosine, thymidine and uracil. The sequences may also contain modified bases such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thioalkyl adenines, 8-hydroxyl adenine and other 8-substituted adenines, 8-halo guanines, 8-amino guanine, 8-thiol guanine, 8-thioalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

The term "suitable for expression in a host cell" means that the recombinant expression vectors contain the chimeric nucleic acid sequence of the invention, a regulatory sequence and a termination region, selected on the basis of the host cells to be used for expression, which is operatively linked to the chimeric nucleic acid sequence. Operatively linked is intended to mean that the chimeric nucleic acid sequence is linked to a regulatory sequence and a termination region in a manner which allows expression of the chimeric sequence. Regulatory sequences and termination regions are art-recognized and are selected to direct expression of the desired protein in an appropriate host cell. Accordingly, the term regulatory sequence includes promoters, enhancers and other expression control elements. Such regulatory sequences are known to those skilled in the art or one described in Goeddel, Gene Expression Technology: Methods in Enzymology 185, Academic Press, San Diego, Calif. (1990) can be used. It should be understood that the design of the expression vector may depend on such factors as the choice of the host cell to be transformed and/or the type of protein desired to be expressed. Such expression vectors can be used to transform cells to thereby produce fusion proteins or peptides encoded by nucleic acids as described herein.

The recombinant expression vectors of the invention can be designed for expression of encoded fusion proteins in prokaryotic or eukaryotic cells. For example, fusion proteins can be expressed in bacterial cells such as *E. coli*, insect cells (using, for example baculovirus), yeast cells, plant cells or mammalian cells. Other suitable host cells can be found in Goeddel, Gene Expression Technology: Methods in Enzymology 185, Academic Press, San Diego, Calif. (1990). The type of host cell which is selected to express the fusion protein is not critical to the present invention and may be as desired.

Expression in prokaryotes is most often carried out in *E. coli* with vectors containing constitutive or inducible promoters directing the expression of the fusion proteins. Inducible expression vectors include pTrc (Amann et al., (1988) Gene 69:301-315) and pET 11d (Studier et al., Gene Expression Technology: Methods in Enzymology 185, Academic Press, San Diego, Calif. (1990) 60-89). While target gene expression relies on host RNA polymerase transcription from the hybrid trp-lac fusion promoter in pTrc, expression of target genes inserted into pET 11d relies on transcription from the T7 gn10-lac 0 fusion promoter mediated by coexpressed viral RNA polymerase (T7 gn1). This viral polymerase is supplied by host strains BL21(DE3) or HMS174(DE3) from a resident λ prophage harboring a T7 gn1 under the transcriptional control of the lacUV 5 promoter. Another attractive bacterial expression system is the pGEX expression system (Pharmacia) in which genes are expressed as fusion products of glutathione-S-transferase (GST), allowing easy purification of the expressed gene from a GST affinity column.

One strategy to maximize recombinant protein expression in *E. coli* is to express the protein in host bacteria with an impaired capacity to proteolytically cleave the recombinantly expressed proteins (Gottesman, S., Gene Expression Technology: Methods in Enzymology 185, Academic Press, San Diego, Calif. (1990) 119-128). Another strategy is to alter the nucleic acid sequence of the chimeric DNA to be inserted into an expression vector so that the individual codons for each amino acid would be those preferentially utilized in highly expressed *E. coli* proteins (Wada et al., (1992) Nuc. Acids Res. 20: 2111-2118). Such alteration of nucleic acid sequences of the invention could be carried out by standard DNA synthesis techniques.

Examples of vectors for expression in yeast *S. cereviseae* include pYepSec1 (Baldari. et al., (1987) Embo J. 6:229-234), pMFa (Kurjan and Herskowitz, (1982) Cell 30:933-943), pJRY88 (Schultz et al., (1987) Gene 54:113-123), and pYES2 (Invitrogen Corporation, San Diego, Calif.).

Baculovirus vectors available for expression of proteins in cultured insect cells (SF 9 cells) include the pAc series (Smith et al., (1983) Mol. Cell Biol. 3:2156-2165) and the pVL series (Lucklow, V. A., and Summers, M. D., (1989) Virology).

Vectors such as the Ti and Ri plasmids are available for transformation and expression of plants. These vectors specify DNA transfer functions and are used when it is desired that the constructs are introduced into the plant and stably integrated into the genome via *Agrobacterium* -mediated transformation.

A typical construct consists, in the 5' to 3' direction, of a regulatory region complete with a promoter capable of directing expression in plant, a protein coding region, and a sequence containing a transcriptional termination signal functional in plants. The sequences comprising the construct may be either natural or synthetic or any combination thereof.

Both non-seed specific promoters, such as the 35-S CaMV promoter (Rothstein et al., (1987), Gene 53: 153-161) and, if seed specific expression is desired, seed-specific promoters such as the phaseolin promoter (Sengupta-Gopalan et al., (1985), PNAS USA 82: 3320-3324) or the *Arabidopsis* 18 kDa oleosin (Van Rooijen et al., (1992) Plant Mol. Biol. 18: 1177-1179) promoters may be used. In addition to the promoter, the regulatory region contains a ribosome binding site enabling translation of the transcripts in plants and may also contain one or more enhancer sequences, such as the AMV leader (Jobling and Gehrke, (1987), Nature 325: 622-625), to increase the expression of product.

The coding region of the construct will typically be comprised of sequences encoding a pro-peptide region fused in frame to a desired protein and ending with a translational termination codon. The sequence may also include introns.

The region containing the transcriptional termination signal may comprise any such sequence functional in plants such as the nopaline synthase termination sequence and additionally may include enhancer sequences to increase the expression of product.

The various components of the construct are ligated together using conventional methods, typically into a pUC-based vector. This construct may then be introduced into an *Agrobacterium* vector and subsequently into host plants, using one of the transformation procedures outlined below.

The expression vectors will normally also contain a marker which enables expression in plant cells. Conveniently, the marker may be a resistance to a herbicide, for example glyphosate, or an antibiotic, such as kanamycin, G418, bleomycin, hygromycin, chloramphenicol or the like. The particular marker employed will be one which will permit selection of transformed cells from cells lacking the introduced recombinant nucleic acid molecule.

A variety of techniques is available for the introduction of nucleic acid sequences, in particular DNA into plant host cells. For example, the chimeric DNA constructs may be introduced into host cells obtained from dicotyledonous plants, such as tobacco, and oleaginous species, such as *B. napus* using standard *Agrobacterium* vectors; by a transformation protocol such as that described by Moloney et al., (1989), (Plant Cell Rep., 8: 238-242) or Hinchee et al., (1988), (Bio/Technol., 6: 915-922); or other techniques known to those skilled in the art. For example, the use of T-DNA for transformation of plant cells has received extensive study and is amply described in EPA Serial No. 120,516; Hoekema et al., (1985), (Chapter V, In: *The Binary Plant Vector System* Offset-drukkerij Kanters B.V., Alblasserdam); Knauf, et al., (1983), (*Genetic Analysis of Host Range Expression by Agrobacterium,* p. 245, In Molecular Genetics of the Bacteria-Plant Interaction, Puhler, A. ed., Springer-Verlag, NY); and An et al., (1985), (EMBO J., 4: 277-284). Conveniently, explants may be cultivated with *A. tumefaciens* or *A. rhizogenes* to allow for transfer of the transcription construct to the plant cells. Following transformation using *Agrobacterium* the plant cells are dispersed in an appropriate medium for selection, subsequently callus, shoots and eventually plantlets are recovered. The *Agrobacterium* host will harbour a plasmid comprising the vir genes necessary for transfer of the T-DNA to the plant cells. For injection and electroporation, (see below) disarmed Ti-plasmids (lacking the tumour genes, particularly the T-DNA region) may be introduced into the plant cell.

The use of non *Agrobacterium* techniques permits the use of the constructs described herein to obtain transformation and expression in a wide variety of monocotyledonous and dicotyledonous plants and other organisms. These techniques are especially useful for species that are intractable in an *Agrobacterium* transformation system. Other techniques for gene transfer include biolistics (Sanford, (1988), Trends in Biotech., 6: 299-302), electroporation (Fromm et al., (1985), Proc. Natl. Acad. Sci. USA, 82: 5824-5828; Riggs and Bates, (1986), Proc. Natl. Acad. Sci. USA 83: 5602-5606) or PEG-mediated DNA uptake (Potrykus et al., (1985), Mol. Gen. Genet., 199: 169-177).

In a specific application, such as to *B. napus,* the host cells targeted to receive recombinant DNA constructs typically will be derived from cotyledonary petioles as described by Moloney et al., (1989, Plant Cell Rep., 8: 238-242). Other examples using commercial oil seeds include cotyledon transformation in soybean explants (Hinchee et al., (1988). Bio/Technology, 6: 915-922) and stem transformation of cotton (Umbeck et al., (1981), Bio/Technology, 5: 263-266).

Following transformation, the cells, for example as leaf discs, are grown in selective medium. Once shoots begin to emerge, they are excised and placed onto rooting medium. After sufficient roots have formed, the plants are transferred to soil. Putative transformed plants are then tested for presence of a marker. Southern blotting is performed on genomic DNA using an appropriate probe, for example a chymosin pro-sequence, to show that integration of the desired sequences into the host cell genome has occurred.

Transformed plants grown in accordance with conventional ways, are allowed to set seed. See, for example, McCormick et al. (1986, Plant Cell Reports, 5: 81-84). Northern blotting can be carried out using an appropriate gene probe with RNA isolated from tissue in which transcription is expected to occur, such as a seed embryo. The size of the transcripts can then be compared with the predicted size for the fusion protein transcript.

Two or more generations of transgenic plants may be grown and either crossed or selfed to allow identification of plants and strains with desired phenotypic characteristics including production of recombinant proteins. It may be desirable to ensure homozygosity of the plants, strains or lines producing recombinant proteins to assure continued inheritance of the recombinant trait. Methods of selecting homozygous plants are well know to those skilled in the art of plant breeding and include recurrent selfing and selection and anther and microspore culture. Homozygous plants may also be obtained by transformation of haploid cells or tissues followed by regeneration of haploid plantlets subsequently converted to diploid plants by any number of known means, (e.g.: treatment with colchicine or other microtubule disrupting agents).

The polypeptide of the present invention may be any polypeptide that is not normally fused to the pro-peptide used in the method. The polypeptide is preferentially stable under cleavage conditions, for example at acidic pH, and the polypeptide may be activated after cleavage upon adjusting the pH, or altering the environment otherwise so that conditions optimal for enzymatic activity are generated. The cleavage reaction may be performed any time upon commencement of the production of the fusion protein in a recombinant cell system. In preferred embodiments the cleavage reaction is performed using crude cellular extracts producing the recombinant protein or any purified fraction thereof.

The pro-peptide used in the present invention may be any pro-peptide derived from any autocatalytically maturing zymogen, including those pro-peptides derived from proteases, including aspartic proteases, serine proteases and cysteine proteases. In preferred embodiments of the invention, the pro-peptide is derived from chymosin, pepsin, HIV-1 protease, pepsinogen, cathepsin or yeast proteinase A. The amino acid and/or DNA sequences of pepsinogen (Ong et al. (1968), J. Biol. Chem. 6104-6109; Pedersen et al., (1973), FEBS Letters, 35: 255-526), chymosin (Foltmann et al., (1977); Harris et al., (1982), Nucl. Acids. Res., 10: 2177-2187), yeast proteinase A (Ammerer et al., (1986), Mol. Cell. Biol. 6: 2490-2499; Woolford et al., (1986), Mol. Cell. Biol. 6: 2500-2510), HIV-1 protease (Ratner et al., (1987), AIDS Res. Human Retrovir. 3: 57-69.), cathepsin (McIntyre et al., (1994), J. Biol. Chem. 269: 567-572) and pepsin are available (Koelsch et al. (1994), FEBS Lett. 343: 6-10). Based on these sequences cDNA clones comprising the genetic material coding for the pro-peptides may be prepared and fusion genes may be prepared in accordance with the present invention and practicing techniques commonly known to those skilled in the art (see e.g. Sambrook et al. (1990), Molecular Cloning, 2nd Ed., Cold Spring Harbor Press).

To identify other pro-sequences having the desired characteristics, where a zymogen undergoing autocatalytic cleavage has been isolated (for example chymosin and yeast protein A), the protein may be partially sequenced, so that a nucleic acid probe may be designed to identify other pro-peptides. The nucleic acid probe may be used to screen cDNA or genomic libraries prepared from any living cell or virus. Sequences which hybridize with the probe under stringent conditions may then be isolated.

Other pro-sequences may also be isolated by screening of cDNA expression libraries. Antibodies against existing pro-peptides may be obtained and cDNA expression libraries may be screened with these antibodies essentially as described by Huynh et al. (1985, in DNA cloning Vol. 1, a Practical Approach, ed. D. M. Glover, IRL Press). Expression libraries may be prepared from any living cell or virus.

Other zymogens which are autocatalytically processed may be discovered by those skilled in the art. The actual pro-sequence which is selected is not of critical importance and may be as desired. It is to be clearly understood that the pro-sequence of any autocatalytically maturing zymogen may be employed without departing from the spirit or scope of the present invention.

Upon isolation of a pro-sequence, the pro-peptide encoding genetic material may be fused to the genetic material encoding polypeptide of interest using DNA cloning techniques known to skilled artisans such as restriction digestion, ligation, gel electrophoresis, DNA sequencing and PCR. A wide variety of cloning vectors are available to perform the necessary cloning steps. Especially suitable for this purpose are the cloning vectors which include a replication system that is functional in *E. coli* such as pBR322, the pUC series, M13mp series, pACYC184, pBluescript etc. Sequences may be introduced into these vectors and the vectors may be used to transform the *E. coli* host, which may be grown in an appropriate medium. Plasmids may be recovered from the cells upon harvesting and lysing the cells.

The invention also includes the full length pro-peptide as well as functional portions of the pro-peptide or functional mutated forms of the pro-peptide. Mutated forms of the pro-peptide may be used to obtain specific cleavage between the pro-peptide and a heterologous protein. Mutations in the pro-peptide could alter the optimal conditions, such as temperature, pH and salt concentration, under which cleavage of a heterologous peptide is achieved (McCaman, M. T. and Cummings, D. B., (1986), J. Biol. Chem. 261:15345-15348). Depending on the pro-peptide, cleavage of the heterologous protein from various pro-peptides, will be optimal under varying different conditions. Thus the invention will be amenable to heterologous proteins which are preferentially cleaved under a variety of desirable conditions.

As described in Example 4, a number of mutated forms of chymosin pro-peptides have been created. The purpose of mutating the chymosin pro-peptides was to test to robustness and flexibility of the system. A number of specific mutations were tested including KLIP 4 (SEQ ID NO:6), KLIP 11 (SEQ ID NO:7), KLIP 12 (SEQ ID NO:8), KLIP 14 (SEQ ID NO:9), and KLIP 15 (SEQ ID NO:10). It should be noted that KLIP 16 (SEQ ID NO:11), the negative control, was not a functional pro-peptide. The results described in Example 4 demonstrate that the chymosin pro-peptide sequence can be mutated and still function in the method of the invention provided that the peptide sequence GISSKF (SEQ ID NO:10) is present in the chymosin pro-peptide.

The nucleic acid sequence encoding the heterologous polypeptide may be fused upstream or downstream of the nucleic acid sequence encoding the pro-peptide and concatamers containing repetitive units of the pro-peptide fused to the heterologous protein may be employed. In preferred embodiments, the heterologous protein is fused downstream of the pro-peptide. The nucleic acid sequence encoding the pro-peptide generally does not include the mature form of the zymogen.

In one embodiment, the pro-peptide is a pro-peptide derived from chymosin and the heterologous polypeptide is hirudin (Dodt et al., (1984), FEBS Letters 65:180-183). In particular, the present inventors have constructed a chimeric DNA sequence in which the DNA encoding the chymosin pro-peptide was fused upstream of the DNA sequence encoding the leech anticoagulant protein hirudin. The gene fusion (Pro-Hirudin) was expressed in *E. coli* cells. It was found that upon lowering of the pH to pH 2, and more preferably to pH 4.5, and in the presence of a small quantity of mature chymosin, the heterologously fused protein, hirudin, was efficiently cleaved from the chymosin pro-peptide.

Autocatalytic cleavage requires an alteration of the environment of the fusion peptide. This may include alterations in pH, temperature, salt concentrations, the concentrations of other chemical agents or any other alteration resulting in environmental conditions that will permit autocatalytic cleavage of the fusion protein. The environment may be altered by the delivery of the fusion protein into an appropriate cleavage environment. The cleavage environment may be a physiological environment, such as for example in the mammalian stomach, gut, kidneys, milk or blood, or the environmental conditions may be man-made. The cleavage environment may also be generated by the addition of an agent or agents or by altering the temperature of the environment of the fusion protein. The cleavage reaction may take place when the fusion protein is pure or substantially pure, as well as when it is present in cruder preparations, such as cellular extracts.

In a preferred embodiment, the inventors have employed mature chymosin to assist in the cleavage reaction. Generally, the addition of the mature enzyme will assist in the cleavage reaction. The enzyme used for this reaction may be homologous to the pro-peptide, for example, chymosin may be used to assist cleavage of pro-chymosin fused to a desired protein, or heterologous to the pro-peptide, for example, pepsin may be used to assist in cleavage of a pro-chymosin fused to a desired protein.

Although in a preferred embodiment mature chymosin is added, it is conceivable that the use of other pro-peptides may not require the addition of the mature peptide in order to accomplish efficient cleavage.

Activation of the fusion protein may be in vitro or in vivo. In one embodiment, the pro-peptide is used to facilitate cleavage from proteins recombinantly produced on oil bodies as disclosed in PCT application Publication No. WO 96/21029. In this embodiment, the pro-peptide would be fused downstream of an oil body protein and upstream of the recombinant protein or peptide of interest.

In another in vivo application, two vectors would be introduced in the same host. In one vector expression of the zymogen or the mature protein would be controlled by an inducible promoter system. The other vector would comprise a pro-peptide fused upstream of a heterologous protein of interest. Thus it is possible to control the moment of cleavage of the peptide or protein downstream of the pro-peptide through the promoter which controls expression of the zymogen or the mature protein. Alternatively, the two expressed genes would be combined in the same vector. In preferred embodiments of this application, the pro-peptide employed is cleaved under physiological conditions.

In another aspect the present invention provides a fusion protein comprising (a) a pro-peptide derived from an autocatalytically maturing zymogen and (b) a polypeptide that is heterologous to the pro-peptide. In one embodiment, the polypeptide is a therapeutic or nutritional peptide or protein which can be administered as an inactive fusion protein. Activation or maturation through cleavage would only occur upon its delivery at the unique physiological conditions prevalent at the target organ, tissue or bodily fluid for example in the mammalian stomach, gut, kidneys, milk or blood. Cleavage might be enhanced by a protease specific for the peptide, preferably the mature zymogen homologous to the pro-peptide is used. This method is particularly useful for the delivery of orally ingested vaccines, cytokines, gastric lipase, peptide antibiotics, lactase and cattle feed enzymes which facilitate digestion, such as xylanase and cellulase. For example, a therapeutic or nutritional peptide or protein fused downstream of the chymosin pro-peptide might be activated in the mammal stomach upon ingestion. The mature form of chymosin or the inactive precursor form of chymosin may be added to assist in the cleavage of the nutritional or therapeutic peptide.

Accordingly, in one embodiment the present invention provides a pharmaceutical composition comprising a fusion protein which comprises (a) a pro-peptide derived from an autocatalytically maturing zymogen and (b) a polypeptide that is heterologous to the pro-peptide in admixture with a suitable diluent or carrier. The composition may be administered orally, intravenously or via any other delivery route.

The fusion protein and/or mature protein may also be produced in an edible food source, such as animal milk or in an edible crop, which may be consumed without a need for further purification. Accordingly, in another embodiment the present invention provides a food composition comprising a fusion protein which comprises (a) a pro-peptide derived from an autocatalytically maturing zymogen and (b) a polypeptide that is heterologous to the pro-peptide in admixture with a suitable diluent or carrier. The nutritional composition may be mixed with any liquid or solid food and consumed by a human or animal.

The compositions of the invention may include the chimeric nucleic acid sequences or an expression vector containing the chimeric nucleic acid sequences of the present invention. In such an embodiment, the fusion protein is produced in vivo in the host animal. The chimeric nucleic acid sequences of the invention may be directly introduced into cells or tissues in vivo using delivery vehicles such as retroviral vectors, adenoviral vectors and DNA virus vectors. The chimeric nucleic acid sequences may also be introduced into cells in vitro using physical techniques such as microinjection and electroporation or chemical methods such as co-precipitation and incorporation of nucleic acid into liposomes. Expression vectors may also be delivered in the form of an aerosol or by lavage.

The present invention is also useful in the purification process of recombinant proteins. In one embodiment, a cell extract containing an expressed pro-peptide-heterologous fusion protein is applied to a chromatographic column. Selective binding of the fusion protein to antibodies raised against the pro-peptide sequence and immobilized onto the column, results in selective retention of the fusion protein. Instead of relying on antibodies against the pro-peptide sequence, a gene encoding another immunogenic domain or a gene encoding a peptide with affinity for a commonly used column material, such as cellulose, glutathione-S-transferase or chitin, or any other desirable tag, may be included in the gene fusion.

In another envisaged application, a peptide encoding a sequence which results in anchoring of the fusion protein in the cell wall would be included in the construct. Suitable anchoring proteins for this application would be yeast $\alpha$-glutenin FLO1, the Major Cell Wall Protein of lower eukaryotes, and a proteinase of lactic acid bacteria (PCT 94/18330) Expression of a fusion protein would result in immobilization of the protein of interest to cell wall. The protein of interest could be isolated by washing the cells with water or washing buffer. Upon cleavage the cells could be removed using a simple centrifugation step and the protein could be isolated from the washing buffer.

The following non-limiting examples are illustrative of the present invention.

EXAMPLES

Example 1

In the first example, the protein hirudin was prepared as a fusion protein with the chymosin pro-peptide and hirudin was shown to be active in cellular extracts of *E. coli* upon performance of a cleavage reaction.

Construction of a pGEX-Pro-Hirudin Fusion

The fusion protein that we studied comprises the pro-peptide of calf chymosin B (Foltmann et al, 1977; Harris et al., 1982, Nucl. Acids. Res., 10: 2177-2187) fused to hirudin variant 1 (Dodt et al., 1984, FEBS Letters 65: 180-183). The hybrid gene which encoded this fusion protein was constructed using standard PCR methods (Horton et al., 1989, Gene, 77: 61-68). The DNA sequence for this Pro-Hirudin fusion was cloned into pGEX-4T-3 (Pharmacia), downstream of the gene encoding glutathion-S-transferase (GST). The complete sequence of the GST-Pro-Hirudin sequence is shown in FIG. 1.

Growth of *E. coli* Transformed with pGEX4T-3 and pGEX-Pro-Hirudin

Plasmids pGEX-4T-3 and pGEX-Pro-Hirudin were transformed into *E. coli*. strain DH5α to allow for high level of expression. A single colony was used to inoculate 5 ml LB-amp broth. These cultures were grown overnight. One ml of each overnight culture was used to inoculate 50 ml of LB-amp broth. These cultures were grown until $OD_{600}$=0.6. At this OD, IPTG (final concentration 1 mM) was added to induce the expression of the GST and GST-Pro-Hirudin fusion proteins. After this induction, the cultures were grown for an additional 3 hours at 37° C. The cells were pelleted at 5000×g for 10 minutes, and resuspended in 5 ml Tris Buffered Saline (TBS). The resuspended cells were sonicated and centrifuged at 12000×g for 15 minutes to separate the inclusion bodies (pellet fraction) from the soluble proteins (supernatant fraction). Western blotting of both the pellet and supernation fraction indicated that under the growing conditions described above, significant amounts (5-10%) of the GST and GST-Pro-Hirudin protein were found in the supernatant fraction. The rest (90-95%) accumulated in inclusion bodies (results not shown).

Hirudin Activity Measurements

The supernatant fractions of both the GST and GST-Pro-Hirudin were tested for anti-thrombin activity. The samples were treated as follows:

A) 20 µl supernatant+20 µl water B) 20 µl supernatant+20 µl of 100 mM Sodium Phosphate pH 2.0 C) 20 µl supernatant+20 µl of 100 mM Sodium Phosphate pH 2.0+2 µg chymosin (Sigma) D) 20 µl supernatant+20 µl of 100 mM Sodium Phosphate pH 4.5 E) 20 µl supernatant+20 µl of 100 mM Sodium Phosphate pH 4.5+2 µg chymosin. These samples were incubated at room temperature for 1 hour. A total of 10 µl of the samples was added to 1 ml assay buffer (20 mM Tris [pH 7.5], 100 mM NaCl, 5 mM $CaCl_2$, 0.1 unit of thrombin) and incubated for 2-3 minutes before the addition of 50 µl p-tos-gly-pro-arg-nitroanilide (1 mM). Thrombin activity was measured as a function of chromozyme cleavage by monitoring the increase in absorption at 405 nm over time (Chang, 1983, FEBS Letters, 164: 307-313). The $\Delta_{Abs}$ (405 nm) was determined after 2 minutes. The result of the activity measurements are indicated in Table 1.

As can be seen from Table 1, the only extract which exhibited significant anti-thrombin activity was the extract containing the GST-Pro-Hirudin fusion which was treated at pH 4.5 and supplemented with 2 µg chymosin (E). Western blotting (results not shown) indicated that apart from treatment at pH 4.5, complete cleavage was also observed when the GST-Pro-Hirudin fusion which was treated at pH 2.0 and supplemented with 2 µg chymosin. It has been well documented that unprocessed chymosin when exposed at pH 2.0, forms a pseudochymosin, before it matures into chymosin (Foltmann et al., 1977, Scand. J. Clin. Lab. Invest. 42: 65-79; Foltmann, 1992, Proc. Natl. Acad. Sci. 74: 2321-2324; McCaman and Cummings, 1988, J. Biol. Chem. 261: 15345-15348) The pseudo chymosin cleavage site is located between the $Phe^{27}$-$Leu^{28}$ peptide bond and is indicated in FIG. 1. The inability of the GST-Pro-Hirudin fusion, which was treated at pH 2.0 and supplemented with 2 µg chymosin, to inhibit thrombin activity might be explained by the fact that cleavage occurred at the $Phe^{27}$-$Leu^{28}$ peptide bond rather than at the $Phe^{43}$-$Val^{44}$ peptide bond which separates the chymosin pro-peptide from the mature hirudin. It has been well documented that (Loison et al., 1988, Bio/Technology, 6: 72-77) mature hirudin is only active when it does not have any additional amino acids attached to its native N-terminal sequence.

Example 2

In the second example, the protein carp growth hormone (cGH) was prepared as a fusion of pro-chymosin. Carp growth hormone was shown to be present in cellular extracts of *E. coli* upon performance of the cleavage reaction.

Construction of a pHis-Pro-cGH Fusion

A fusion protein was constructed which comprises the pro-peptide of calf chymosin B (Foltmann et al., (1977), Harris et al., 1982, Nucl. Acids Res. 10: 2177-2187 fused to carp growth hormone (Koren et al. (1989), Gene 67: 309-315). The hybrid gene which encoded this fusion protein was constructed using PCR mediated gene-fusion. The DNA sequence for this Pro-cGH fusion was cloned into pUC19 yielding plasmid pPro-cGH. The Pro-cGH gene fusion was released from pPro-cGH by SwaI/KpnI digestion and inserted into the PvuII/KpnI site of pRSETB (Invitrogen Corp.), containing a poly-histidine tag, facilitating purification, and an enterokinase recognition and cleavage site to generate pHis-Pro-cGH. The complete sequence of the His-Pro-cGH insert is shown in FIG. 2.

Growth of *E. coli* Transformed with pHis-Pro-cGH

Plasmid pHis-Pro-cGH was transformed into *E. coli* BL21 strain to allow for high levels of expression. A single colony was used to inoculate LB-amp broth These cultures were grown overnight. One ml of each o/n culture was used to inoculate 50 ml of LB-amp broth. These cultures were grown until $OD_{600}$=0.6. At this OD, IPTG (final concentration 0.5 mM) was added to induce the expression of the His-Pro-cGH fusion protein. After this induction, the cultures were grown for an additional 3 hours at 37° C. The cells were pelleted at 5000×g for 10 minutes, and resuspended in 5 ml PBS (pH 7.3) buffer. The resuspended cells were disrupted by a French-Press and centrifuged at 10,000×g for 10 minutes. Inclusion bodies were resuspended in 5 ml of water and dissolved by slow addition of NaOH. 1 ml of 10×PBS was added to this solution and the volume was adjusted to 10 ml. The pH of the solution was adjusted to 8.0 by slow addition of HCl and the solution was incubated at 4° C. for 2 hours. The pH wasadjusted to 7.5 and at this point the solution was centrifuged at 10,000 g for 15 minutes to remove insolubles.

The fusion protein was then purified by chelating affinity chromatography using Hi-Trap metal binding columns (Pharmacia). The column was saturated with $Zn^{++}$ ions and then used to affinity purify His-Pro-cGH fusion protein in accordance with the instructions provided by the manufacturer.

Cleavage of cGH Produced in E. coli Transformed with pHis-Pro-cGH

In order to cleave the fusion protein 15 µl (ca 1 µg) of the protein prep was treated with either 17 µl of PBS (Uncut), 14 µl of PBS and 3 µl of enterokinase (Cut (EK)), or 16 µl of phosphate buffer (pH 2) and 1 µl of chymosin (Cut (PRO)). All samples were incubated at 37° C. for 2 hours and then analysed by SDS-PAGE followed by western blotting. The primary antibody used was a rabbit anti-serum prepared against cGH. The secondary antibody was goat anti-rabbit IgG which was conjugated with alkaline phosphatase.

As can be seen from FIG. 3, cleavage of the fusion protein was observed with enterokinase yielding a protein band corresponding to the calculated molecular mass of the Pro-cGH fusion (26 kDa). Similarly the cleavage with chymosin yielded a protein band corresponding to the expected theoretical molecular mass of the cGH (approximately 22 kDa) polypeptide.

Example 3

In this example, the protein carp growth hormone (cGH) was prepared as a fusion of pro-chymosin. The carp growth hormone fusion protein was cleaved with the gut extract from red turnip beetle, thus illustrating an in vivo application of the invention.

His-Pro-cGH was prepared following the protocol of example 2. Gut extract was prepared from larvae of the red turnip beetle as follows. Red turnip beetle eggs (*Entomoscelis americana* Brown (Coleoptera: Chrysomelidae), were laid by laboratory-reared adults and stored at −20° C. for at least three months before use. Eggs were hatched in dishes containing moist filter paper, and larvae were maintained on canola seedlings. Only larvae that were actively feeding were used. Midguts from second instar larvae were removed by dissection in saline solution and stored in saline at −20° C. Guts were thawed, rinsed in $ddH_2O$ (50 µl per gut). The homgenate was centrifuged at 16,000×g (10 min, 4° C.) and the decanted supernatant was used in the proteolyic assay.

Figure 4:
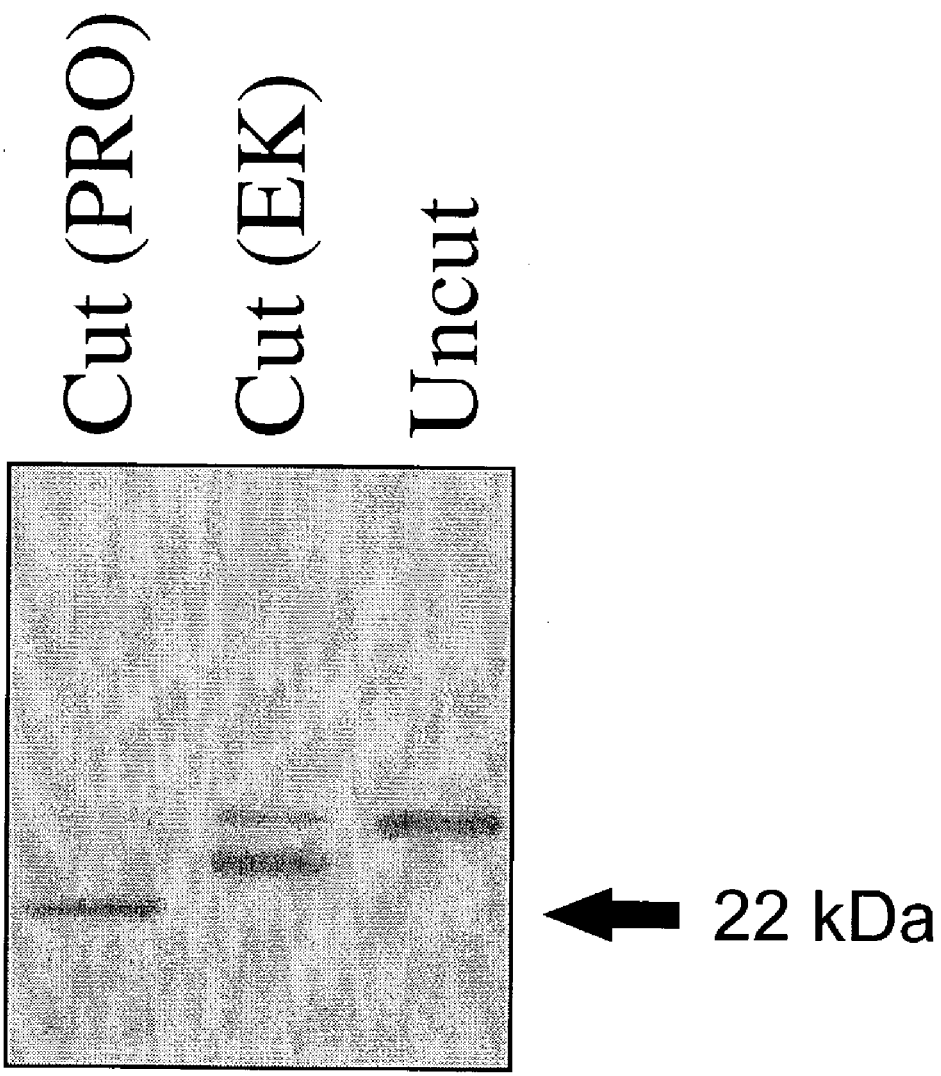
FIG. 4 illustrates the in vitro cleavage of purified His-Pro-cGH.

As can be observed in FIG. 4, extracts prepared from the gut of red turnip beetle cleaved the fusion protein and released the cGH polypeptide. Cleavage was not observed to be complete. This could be due to the fact that the pH in the gut extract was not optimal for the cleavage reaction to proceed.

Example 4

Heterologous Cleavage of Chymosin Pro-Peptide N Terminal Deletions

This example outlines the enzymatic cleavage of a glutathione-S-transferase (GST)-cystatin fusion with intervening pro-peptides derived from chymosin. The purpose of mutating the chymosin pro-peptides was to test to robustness and flexibility of the system. Each of the pro-peptides used in the current example are mutated forms with varying levels of functionality. The pro-peptides are designed as proteolytically cleavable targets for calf chymosin and are designated as KLIP peptides in the current example (FIG. 6). The recombinant expression of GST-KLIP-Cystatin fusions was isolated from the cellular extracts of E. coli and subsequently purified with Glutathione Sepharose 4B. Purified extracts were enzymatically cleaved with mature chymosin. Cleaved polypeptide products bearing the same molecular mass as cystatin were correctly identified as cystatin polypeptides by Western Blot analysis and N-terminal sequencing verified accurate cleavage had occurred.

Construction of a pGEX-KLIP-Cystatin Fusion

The fusion proteins studied represent derivatives of the pro-peptide of calf chymosin B (Foltmann et al., 1977; Harris et al., 1982, Nucl. Acids Res., 10:2177-2187) fused to cystatin (Chen et al, 1992). The hybid genes which encoded these fusion proteins were constructed using standard PCR methods (Horton et al., 1989, Gene, 77:61-68). The DNA sequences encoding for the KLIP-Cystatin fusions were cloned in-frame into pGEX-4T-3 (Pharmacia Biotech), downstream of the gene encoding for glutathione-S-transferase (GST). The complete sequences of the chymosin pro-peptide mutants (GST-KLIP-Cystatin) are shown in FIGS. 7 through 12.

Growth of E. coli Transformed with pGEX-4T-3 and pGEX-KLIP-Cystatin

Plasmids pGEX-4T-3 and pGEX-KLIP-Cystatin were transformed into E. coli strain BL21. A single recombinant colony was used to inoculate 5 ml LB broth with 100 µg/ml ampicillin. The cultures were incubated at 37° C., shaking at 225 rpm, overnight. Overnight cultures were diluted 1:10 into fresh pre-warmed LB broth plus 100 µg/ml Ampicillin and grown at 37° C., with shaking at 225 rpm, until the A600 reached between 1.0-2.0. Thereafter, 100 mM IPTG was added to a final concentration of 0.4 mM to induce expression of the GST and GST-KLIP-Cystatin and incubated at 37° C. for an additional 2-6 hrs. Cells were pelleted at 5000×g for 10 min at 4° C., the supernatant drained and the cells resuspended in ice-cold phosphate buffered saline (PBS; 50 µl/ml of culture). Cells were disrupted by sonicating on ice in short bursts until partial clearing of the suspension occurred. Triton X-100 (20%) was added to a final concentration of 1% and mixed gently at room temperature for 30 min to aid in solubilization of the GST-KLIP-Cystatin fusion protein. The slurry was then centrifuged at 12 000×g for 10 min at 4° C. The supernatant was retrieved and transferred to a clean container. The soluble GST-KLIP-Cystatin fusion protein was then purified using Glutathione Sepharose 4B. Western blotting in combination with Coomassie stained SDS-PAGE revealed the recovery of all GST-KLIP-Cystatin fusion proteins was obtained following elution from glutathione sepharose 4B.

Calf Chymosin Cleavage of Recombinant Cystatin Expressed in E. coli Transformed with cDNA Encoding for KLIP-Cystatin Fusion Protein Cleavage reactions occurred in 100 mM $Na_2HPO_4$, pH 4.0, in the presence of 1:100 calf chymosin:fusion protein ratio. Reactions were incubated for 0, 30, 60, or 120 min at 37° C. or 16 hrs at room temperature and were stopped by the addition of an equal volume of 2×SDS-PAGE loading buffer (125 mM Tris-HCl pH 6.8, 20% glycerol, 4% SDS, 0.2 M DTT, 0.01% bromophenol blue). The proteolytic cleavage products and control reactions were analyzed by SDS-PAGE followed by Coomassie-staining (FIGS. 13-18). The identity of polypeptide bands corresponding to GST-KLIP-Cystatin and freed cystatin was obtained by SDS-PAGE under the same conditions followed by Western Blotting. The primary antibody used was a rabbit anti-serum prepared against cystatin, while the secondary antibody was goat anti-rabbit IgG conjugated with alkaline phosphatase.

As can be seen in FIGS. 13 through 17, the cleavage examples of the fusion protein GST-KLIP-Cystatin, occurred with chymosin at all time points with the exception of the T=0 control. The disappearance of the GST-KLIP-Cystatin polypeptide bands and accumulation of a polypeptide band corresponding to the calculated molecular mass of free cystatin are clearly visible on Coomassie stained SDS-PAGE gels. Both bands denoted in FIGS. 13 through 17 were immuno-reactive with the anti-cystatin polyclonal IgG. The other proteolytic products represent GST and break-down derivatives of GST. Table 2 summarizes the cleavage results obtained for each of the corresponding KLIP peptides summarized in FIGS. 13 through 18 expressed in *E. coli* as GST-KLIP-Cystatin fusion proteins. The samples listed below correspond to the KLIP peptides presented in FIG. 6. The disappearance of fusion protein and accumulation of freed cystatin were determined using densitometry. The N-terminal sequence of the cleavage products was determined by API on a Hewlett Packard G1005A protein sequencer.

Polypeptide bands corresponding to the molecular mass of free cystatin were subjected to N-terminal sequencing to determine the precise location of the scissile bond (Table 2). The N-terminal sequencing was performed by the Alberta Peptide Institute (API, University of Alberta, Edmonton, Alberta, Canada). All KLIP-Cystatin fusions were accurately cleaved with the exception of KLIP 16 (negative control) (FIG. 18), which represents a mutant where the entire chymosin pro-peptide has been deleted. The accurate cleavage of KLIP 15 (FIG. 17) reveals functionality of the pro-peptide is retained in the 6 amino acid portion GISSKF (SEQ ID NO:10).

In conclusion, the chymosin pro-peptide represents a robust and flexible system which is amenable to mutation. As well, the GISSKF (SEQ ID NO:10) portion of the pro-peptide is required for functionality.

While the present invention has been described with reference to what are presently considered to be the preferred examples, it is to be understood that the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

DETAILED FIGURE LEGENDS

FIG. 1. The nucleic acid and deduced amino acid sequence of a GST-Pro-Hirudin sequence. The deduced sequence of the chymosin pro-peptide has been underlined and the deduced hirudin protein sequence has been italicized. The hirudin nucleic acid sequence was optimized for plant codon usage. The pseudochymosin cleavage site between Phe27-Leu28 and the peptide bond separating the pro-chymosin and mature hirudin (Phe 42-Val43) are indicated with an arrow (→).

FIG. 2. The nucleic acid and deduced amino acid sequence of a His-Pro-cGH sequence. The deduced sequence of the chymosin pro-peptide has been underlined and the deduced amino acid of cGH has been italicized. The cleavage site of enterokinase between (Lys31-Asp32) and the peptide bond separating the pro-chymosin and the mature cGH (Phe84-Ser85) are indicated with an arrow (→). The poly-histidine site (His5-His10) and the enterokinase recognition site (Asp27 - Lys31) are also indicated.

FIG. 3 is a schematic diagram of the His-Pro-cGH fusion construct. The enterokinase cleavage site (enterokinase cleavage) and pro-chymosin cleavage site (PRO Cleavage) are indicated with an arrow (→).

FIG. 4 illustrates the cleavage of purified His-Pro-cGH. Shown on the Western blot probed with an anti cGH antibodies are column purified His-Pro-cGH protein extracts from *E. coli* cells expressing the His-Pro-cGH fusion construct treated with enterokinase (Cut (EK)), mature chymosin at low pH (Cut (PRO)) and the control which was treated with PBS buffer (Uncut).

Figure 5:
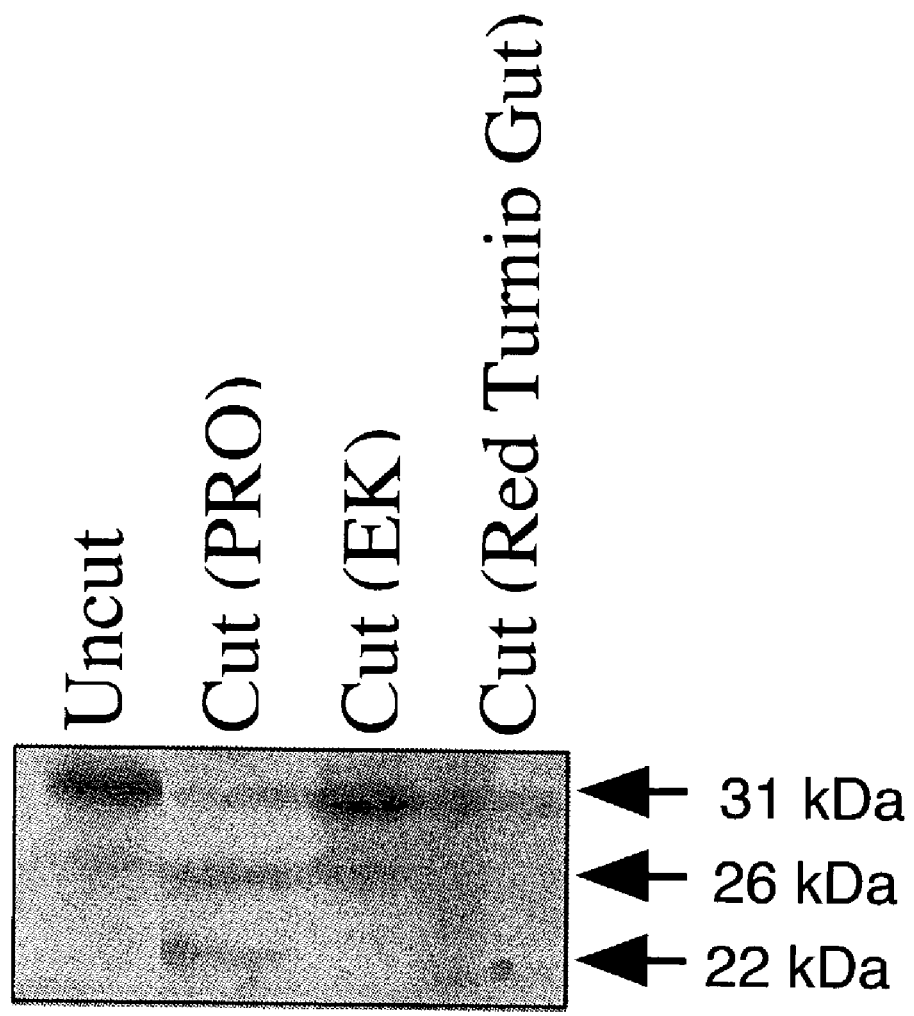
FIG. 5 illustrates the in vivo cleavage of purified His-Pro-cGH.

FIG. 5 illustrates the cleavage of purified His-Pro-cGH. Shown on the Western blot probed with anti cGH antibodies are column purified His-Pro-cGH protein extracts from *E. coli* cells expressing the His-Pro-cGh fusion construct treated with mature chymosin at low pH (Cut (PRO)), treated with enterokinase (Cut (EK)), treated with gut extract from red turnip beetle (Cut (Red Turnip Gut)).

FIG. 6 is an amino acid comparison between wild-type calf chymosin pro-peptide (SEQ.ID.NO.:5), KLIP 4 (SEQ.ID.NO.:6), KLIP 11 (SEQ.ID.NO.:7), KLIP 12 (SEQ.ID.NO.:8), KLIP 14 (SEQ.ID.NO.:9), KLIP 15 (SEQ.ID.NO.: 10), and KLIP 16 (SEQ.ID.NO.:11)

FIG. 7 is the nucleic acid (SEQ.ID.NO.:12) and deduced amino acid sequence (SEQ.ID.NO.:13) of a glutathione S transferase KLIP 4 chymosin pro-peptide cystatin (GST-KLIP4-cystatin) fusion protein. The deduced amino acid sequence of KLIP 4 pro-peptide has been underlined and the deduced cystatin protein sequence has been italicized. The targeted scissile bond for cleavage with calf chymosin between Phe-Met is indicated with an arrow (→).

FIG. 8 is the nucleic acid (SEQ.ID.NO.:14) and deduced amino acid sequence (SEQ.ID.NO.:15) of a glutathione S transferase KLIP 11 chymosin pro-peptide cystatin (GST-KLIP11-cystatin) fusion protein. The deduced amino acid sequence of KLIP 11 pro-peptide has been underlined and the deduced cystatin protein sequence has been italicized. The targeted scissile bond for cleavage with calf chymosin between Phe-Met is indicated with an arrow (→).

FIG. 9 is the nucleic acid (SEQ.ID.NO.:16) and deduced amino acid sequence (SEQ.ID.NO.:17) of a glutathione S transferase KLIP 12 chymosin pro-peptide cystatin (GST-KLIP12-cystatin) fusion protein. The deduced amino acid sequence of KLIP 12 pro-peptide has been underlined and the deduced cystatin protein sequence has been italicized. The targeted scissile bond for cleavage with calf chymosin between Phe-Met is indicated with an arrow (→).

FIG. 10 is the nucleic acid (SEQ.ID.NO.:18) and deduced amino acid sequence (SEQ.ID.NO.:19) of a glutathione S transferase KLIP 14 chymosin pro-peptide cystatin (GST-KLIP14-cystatin) fusion protein. The deduced amino acid sequence of KLIP 14 pro-peptide has been underlined and the deduced cystatin protein sequence has been italicized. The targeted scissile bond for cleavage with calf chymosin between Phe-Met is indicated with an arrow (→).

FIG. 11 is the nucleic acid (SEQ.ID.NO.:20) and deduced amino acid sequence (SEQ.ID.NO.:21) of a glutathione S transferase KLIP 15 chymosin pro-peptide cystatin (GST-KLIP15-cystatin) fusion protein. The deduced amino acid sequence of KLIP 15 pro-peptide has been underlined and the deduced cystatin protein sequence has been italicized. The targeted scissile bond for cleavage with calf chymosin between Phe-Met is indicated with an arrow (→).

FIG. 12 is the nucleic acid (SEQ.ID.NO.:22) and deduced amino acid sequence (SEQ.ID.NO.:23) of a glutathione S transferase KLIP 16 chymosin pro-peptide cystatin (GST-KLIP16-cystatin) fusion protein. The deduced amino acid sequence of KLIP 16 pro-peptide has been underlined and the deduced cystatin protein sequence has been italicized.

Figure 13:
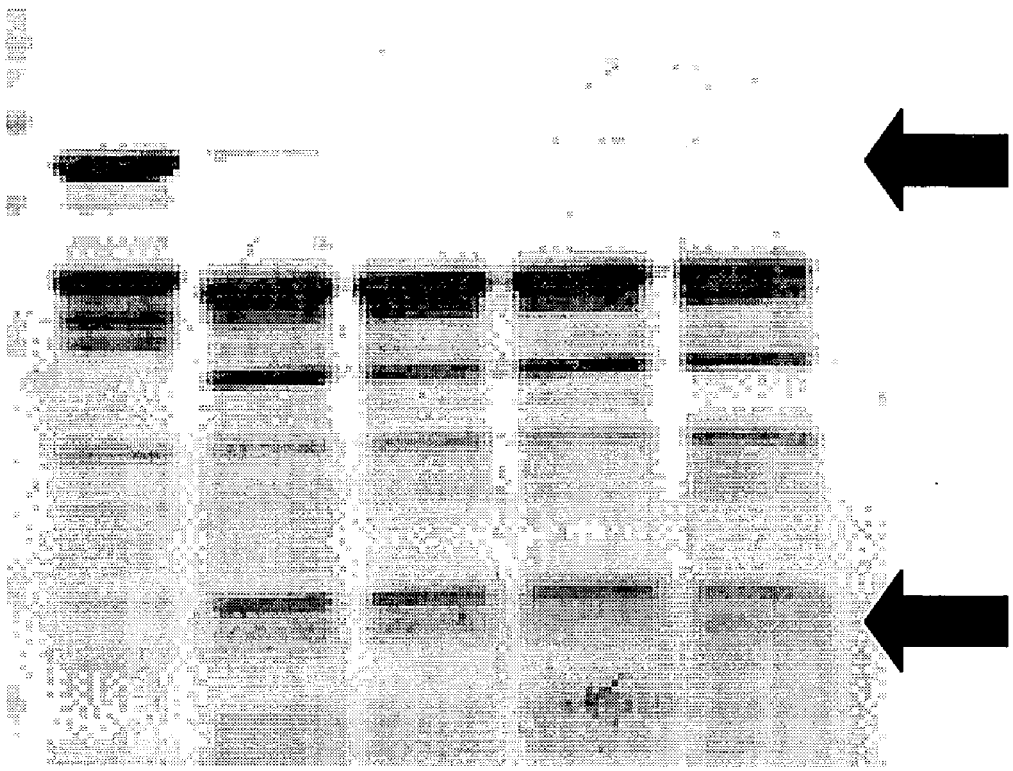
FIG. 13 is a Coomassie Blue stained SDS-PAGE gel denoting the time course cleavage of GST-KLIP4-Cystatin by calf chymosin

FIG. 13 is an example of fusion protein and proteolytic products in Coomassie stained SDS-PAGE. GST-KLIP4-Cystatin was expressed in E. coli and cleaved with calf chymosin as described. Cleavage reactions for 0.5, 1.0, and 2.0 hrs were incubated at 37° C., while the 16 hr incubation was carried out at room temperature (RT). The upper arrow denotes the position of GST-KLIP4-Cystatin and the lower arrow the position of freed cystatin. The identity of these bands was corroborated by Western Blot analysis. The polypeptide band corresponding to cystatin was further characterized by N-terminal sequencing.

Figure 14:
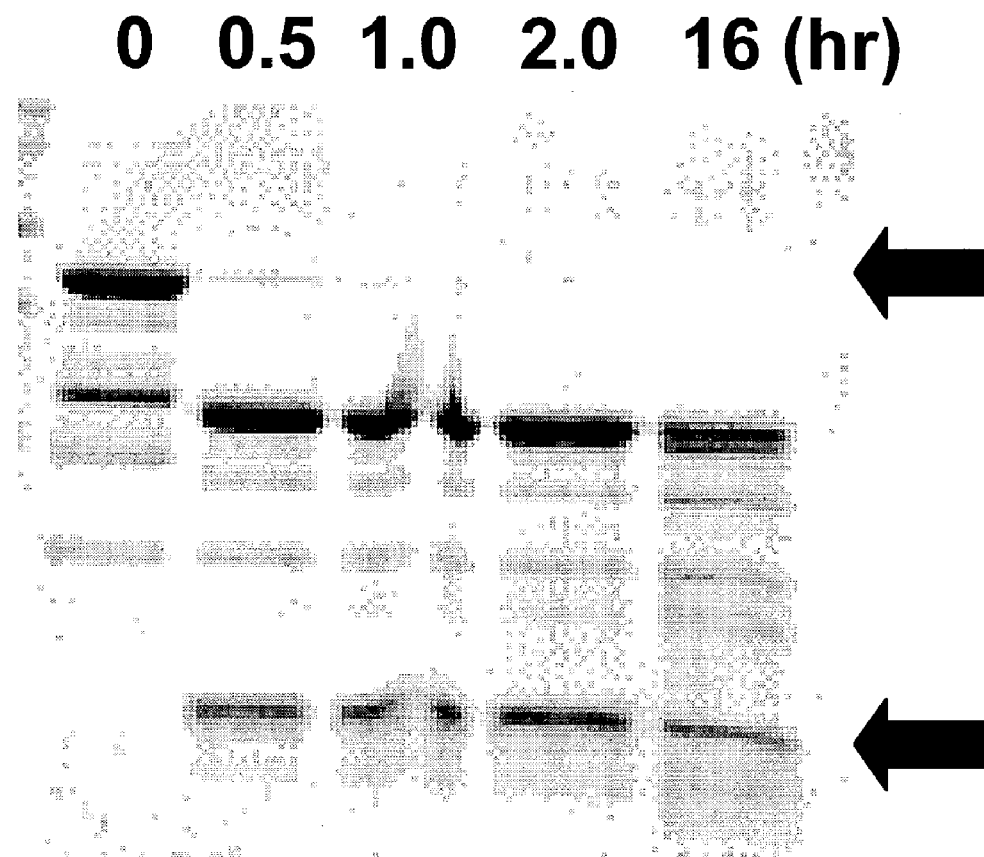
FIG. 14 is a Coomassie Blue stained SDS-PAGE gel denoting the time course cleavage of GST-KLIP11-Cystatin by calf chymosin

FIG. 14 is an example of fusion protein and proteolytic products in Coomassie stained SDS-PAGE. GST-KLIP11-Cystatin was expressed in E. coli and cleaved with calf chymosin as described. Cleavage reactions for 0.5, 1.0, and 2.0 hrs were incubated at 37° C., while the 16 hr incubation was carried out at room temperature (RT). The upper arrow denotes the position of GST-KLIP11-Cystatin and the lower arrow the position of freed cystatin. The identity of these bands was corroborated by Western Blot analysis. The polypeptide band corresponding to cystatin was further characterized by N-terminal sequencing.

Figure 15:
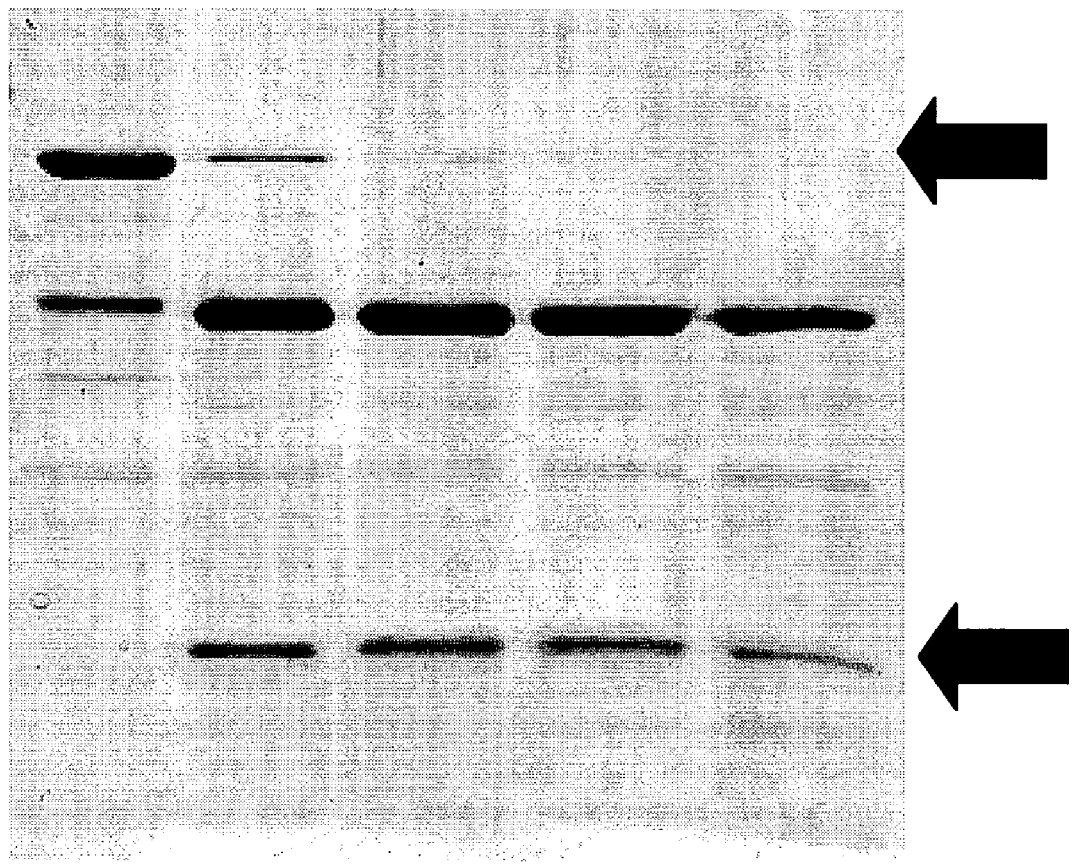
FIG. 15 is a Coomassie Blue stained SDS-PAGE gel denoting the time course cleavage of GST-KLIP12-Cystatin by calf chymosin

FIG. 15 is an example of fusion protein and proteolytic products in Coomassie stained SDS-PAGE. GST-KLIP12-Cystatin was expressed in E. coli and cleaved with calf chymosin as described. Cleavage reactions for 0.5, 1.0, and 2.0 hrs were incubated at 37° C., while the 16 hr incubation was carried out at room temperature (RT). The upper arrow denotes the position of GST-KLIP12-Cystatin and the lower arrow the position of freed cystatin. The identity of these bands was corroborated by Western Blot analysis. The polypeptide band corresponding to cystatin was further characterized by N-terminal sequencing.

Figure 16:
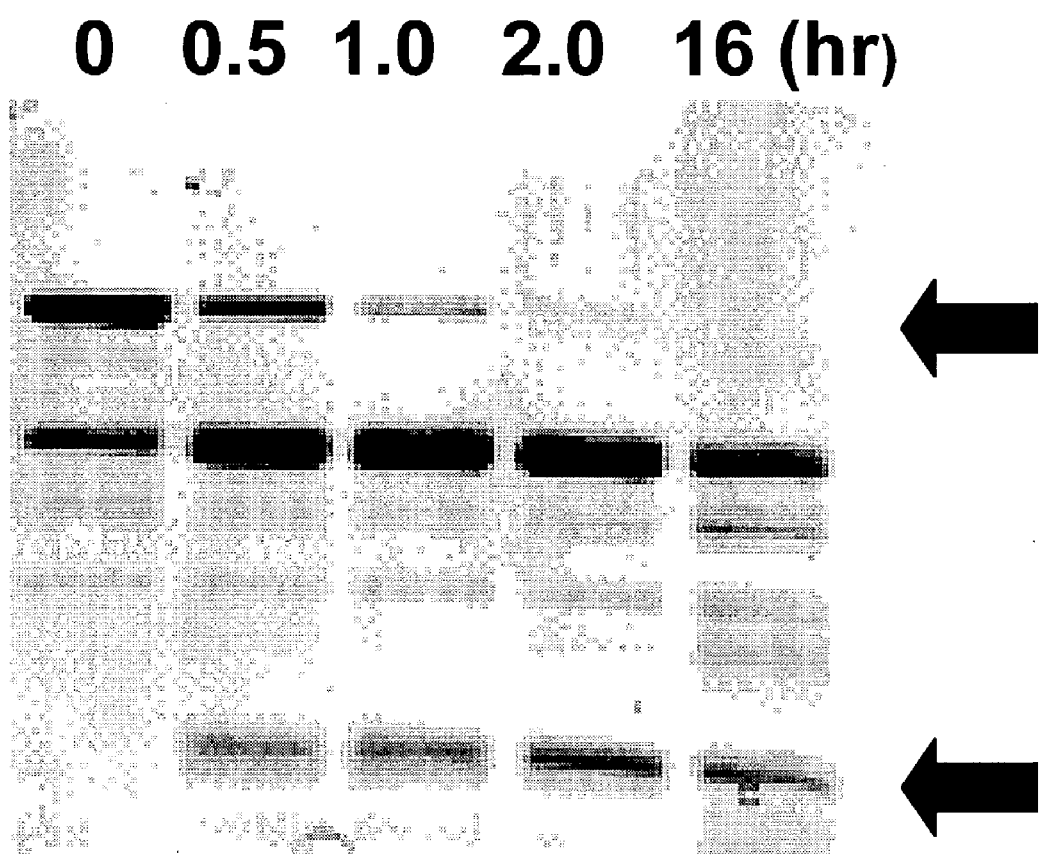
FIG. 16 is a Coomassie Blue stained SDS-PAGE gel denoting the time course cleavage of GST-KLIP14-Cystatin by calf chymosin

FIG. 16 is an example of fusion protein and proteolytic products in Coomassie stained SDS-PAGE. GST-KLIP14-Cystatin was expressed in E. coli and cleaved with calf chymosin as described. Cleavage reactions for 0.5, 1.0, and 2.0 hrs were incubated at 37° C., while the 16 hr incubation was carried out at room temperature (RT). The upper arrow denotes the position of GST-KLIP14-Cystatin and the lower arrow the position of freed cystatin. The identity of these bands was corroborated by Western Blot analysis. The polypeptide band corresponding to cystatin was further characterized by N-terminal sequencing.

Figure 17:
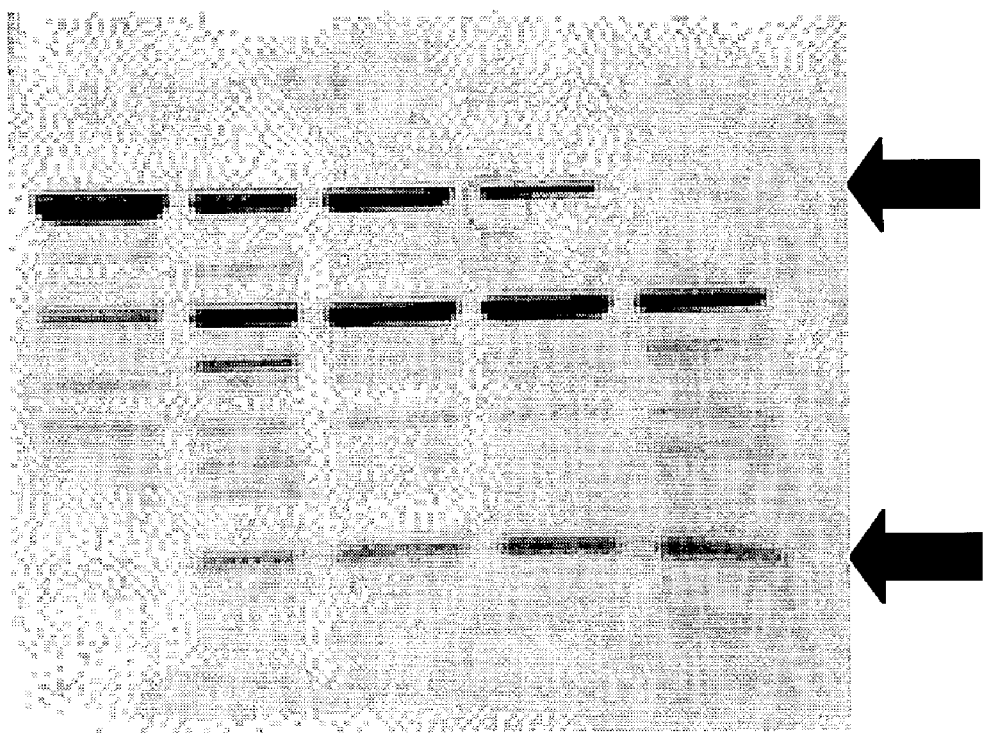
FIG. 17 is a Coomassie Blue stained SDS-PAGE gel denoting the time course cleavage of GST-KLIP15-Cystatin by calf chymosin

FIG. 17 is an example of fusion protein and proteolytic products in Coomassie stained SDS-PAGE. GST-KLIP15-Cystatin was expressed in E. coli and cleaved with calf chymosin as described. Cleavage reactions for 0.5, 1.0, and 2.0 hrs were incubated at 37° C., while the 16 hr incubation was carried out at room temperature (RT). The upper arrow denotes the position of GST-KLIP15-Cystatin and the lower arrow the position of freed cystatin. The identity of these bands was corroborated by Western Blot analysis. The polypeptide band corresponding to cystatin was further characterized by N-terminal sequencing.

Figure 18:
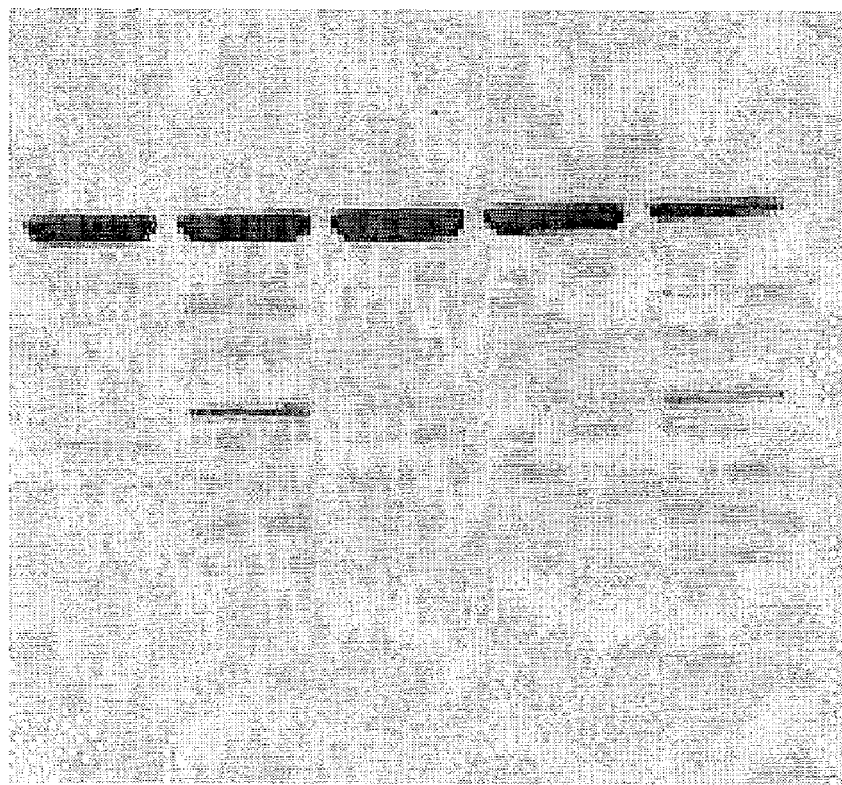
FIG. 18 is a Coomassie Blue stained SDS-PAGE gel denoting the time course cleavage of GST-KLIP16-Cystatin by calf chymosin

FIG. 18 is an example of fusion protein and proteolytic products in Coomassie stained SDS-PAGE. GST-KLIP16-Cystatin was expressed in E. coli and incubated with calf chymosin for 0.5, 1.0, and 2.0 hrs at 37° C., while the 16 hr incubation was carried out at room temperature (RT). The upper arrow denotes the position of GST-KLIP16-Cystatin fusion protein. The identity of these bands was corroborated by Western Blot analysis.

SUMMARY OF SEQUENCES

SEQ.ID.NO.: 1 and SEQ.ID.NO.:2 set forth the nucleic acid and deduced amino acid sequence respectively of a GST-Cymosin pro-peptide-Hirudin sequence (FIG. 1).

SEQ.ID.NO.: 3 and SEQ.ID.NO.:4 set forth the nucleic acid and deduced amino acid sequence respectively of a poly histidine tagged chymosin pro-peptide carp growth hormone (His-Pro-cGH) fusion protein (FIG. 2).

SEQ.ID.NO.: 5 sets forth the amino acid sequence for the wild-type calf chymosin propeptide.

SEQ.ID.NO.: 6-11 set for the amino acid sequences of the mutant calf chymosin propeptides (KLIP 4, KLIP11, KLIP 12, KLIP14, KLIP 15 and KLIP 16).

SEQ.ID.NO.: 12 and SEQ.ID. NO.: 13 set for the nucleic acid and deduced amino acid sequence respectively of a GST-KLIP4-cystatin fusion protein.

SEQ.ID.NO.: 14 and SEQ.ID. NO.: 15 set for the nucleic acid and deduced amino acid sequence respectively of a GST-KLIP11-cystatin fusion protein.

SEQ.ID.NO.: 16 and SEQ.ID. NO.: 17 set for the nucleic acid and deduced amino acid sequence respectively of a GST-KLIP12-cystatin fusion protein.

SEQ.ID.NO.: 18 and SEQ.ID. NO.: 19 set for the nucleic acid and deduced amino acid sequence respectively of a GST-KLIP14-cystatin fusion protein.

SEQ.ID.NO.: 20 and SEQ.ID. NO.: 21 set for the nucleic acid and deduced amino acid sequence respectively of a GST-KLIP15-cystatin fusion protein.

SEQ.ID.NO.: 22 and SEQ.ID. NO.: 23 set for the nucleic acid and deduced amino acid sequence respectively of a GST-KLIP16-cystatin fusion protein.

TABLE 1

Activity measurements of bacterial extracts containing GST (Glutathion-S-transferase) and GST-Pro-Hirudin fusions.

| Sample | Δ Abs (405 nm)/2 min [Test 1] | Δ Abs (405 nm)/2 min [Test 2] |
| --- | --- | --- |
| 1 unit Thrombin | 0.088 | 0.066 |
| A: GST | 0.087 | 0.082 |
| B: GST pH 2.0 | 0.082 | 0.073 |
| C: GST pH 2.0 + 2 μg chymosin | 0.063 | 0.073 |
| D: GST pH 4.5 | 0.087 | 0.086 |
| E: GST pH 4.5 + 2 μg chymosin | 0.087 | 0.087 |
| A: GST-PRO-HIR | 0.076 | 0.071 |
| B: GST-PRO-HIR pH 2.0 | 0.072 | 0.064 |
| C: GST-PRO-HIR pH 2.0 + 2 μg chymosin | 0.066 | 0.070 |
| D: GST-PRO-HIR pH 4.5 | 0.078 | 0.075 |
| E: GST-PROHIR pH 4.5 + 2 μg chymosin | 0.0002 | 0.0001 |
| Hirudin 2 μg | 0.0001 | 0.0001 |

TABLE 2

Results obtained for cleavage of GST-KLIP-Cystatin fusion proteins expressed in *E. coli*.

| Sample | T = 0 | 0.5 hr @ 37° C. | 1.0 hr @ 37° C. | 2.0 hr @ 37° C. | 16 hr @ RT | Scissile bond (N-terminal sequence) |
|---|---|---|---|---|---|---|
| Wild type | 0 | ND | ND | ND | 50 | SGFMSSDGG |
| pro-peptide (SEQ.ID.No.,5 | | | | | 50 | MSSDGG |
| KLIP 4 (SEQ.ID.NO.:6) | 0 | 100 | 100 | 100 | 87 | MSSDGG |
| KLIP 11 (SEQ.ID.NO.7) | 0 | 83 | 80.5 | 100 | 67.8 | MSSDGG |
| KLIP 12 (SEQ.ID.NO.:8) | 0 | 84 | 99.4 | 87 | 64 | MSSDGG |
| KLIP 14 (SEQ.ID.NO.:9) | 0 | 72 | 87 | 99 | 70 | MSSDGG |
| KLIP 15 (SEQ.ID.NO.:10) | 0 | 40 | 57.8 | 77.8 | 85 | MSSDGG |
| KLIP 16 (SEQ.ID.NO.:11) | 0 | 0 | 0 | 0 | 0 | Uncleavable |

We claim:

1. A method for the preparation of a recombinant polypeptide, comprising
    a) transforming a non-human host cell an expression vector comprising:
        (1) a nucleic acid sequence capable of regulating transcription in a host cell, operatively linked to
        (2) a chimeric nucleic acid sequence encoding a fusion protein, wherein said chimeric nucleic acid sequence comprises (a) a nucleic acid sequence encoding a pro-peptide sequence comprising SEQ ID NO:10, linked in reading frame to (b) a nucleic acid sequence that is heterologous to the pro-peptide and that encodes the recombinant polypeptide, wherein the heterologous nucleic acid sequence is located immediately downstream of the nucleic acid sequence encoding the pro-peptide; operatively linked to
        (3) a nucleic acid sequence encoding a termination region functional in said host cell,
    b) growing the host cell to produce said fusion protein;
    c) obtaining said fusion protein from said non-human host cell, and
    d) contacting said fusion protein with a mature form of an autocatalytically maturing aspartic protease that cleaves the pro-peptide, whereby said pro-peptide is cleaved from said fusion protein to release said recombinant polypeptide.

2. A method according to claim 1 wherein said pro-peptide sequence comprises a sequence selected from the group consisting of SEQ ID NO:7, SEQ ID NO:8, SEQ ID NO:9.

3. A method according to claim 1 wherein the recombinant polypeptide is selected from the group consisting of hirudin, carp growth hormone and cystatin.

4. A method according to claim 1 wherein step d) is effected under in vitro conditions.

5. A method according to claim 1 wherein step d) is effected under in vivo conditions.

6. A method according to claim 5 wherein step d) is effected in a tissue, organ, or bodily fluid of an animal.

7. A method according to claim 5 wherein step d) is effected in the milk, blood, the stomach, the gut or the kidneys of said animal.

8. A method according to claim 1 wherein said autocatalytically maturing aspartic protease is chymosin.

9. The method according to claim 8 wherein step d) is effected under in vitro conditions.

10. The method according to claim 8 wherein step d) is effected under in vivo conditions.

11. The method according to claim 10 wherein step d) is effected in a tissue, organ, or bodily fluid of an animal.

12. The method according to claim 11 wherein the tissue, organ, or bodily fluid is a stomach, kidney, gut, blood or milk of said animal.

13. A method according to claim 1 wherein said nucleic acid sequences are deoxyribonucleic acid (DNA) sequences.

14. The method according to claim 1 wherein step d) is effected at a pH of from about 2 to about 4.5.

15. A method for the preparation of a recombinant polypeptide, comprising
    a) transforming a host cell with an expression vector comprising:
        (1) a nucleic acid sequence capable of regulating transcription in a host cell, operatively linked to
        (2) a chimeric nucleic acid sequence that encodes a fusion protein, wherein said chimeric nucleic acid sequence comprises (a) a nucleic acid sequence encoding a pro-peptide sequence comprising SEQ ID NO:10, linked in reading frame to (b) a nucleic acid sequence that is heterologous to the pro-peptide and that encodes the recombinant polypeptide wherein the heterologous nucleic acid sequence is located immediately downstream of the nucleic acid sequence encoding the pro-peptide; operatively linked to (3) a nucleic acid sequence encoding a termination region that is functional in said host cell, wherein the host cell is selected from the group consisting of bacterial cells, yeast cells and plant cells, b) growing the host cell to produce said fusion protein;

c) contacting said fusion protein in vivo with a mature from of an autocatalytically maturing aspartic protease that cleaves the pro-peptide by expressing said autocatalytically maturing aspartic protease in said host cell, whereby said pro-peptide is cleaved from said fusion protein to release recombinant polypeptide.

16. The method according to claim 15, wherein said autocatalytically maturing aspartic protease is chymosin.

17. The method according to claim 15 wherein said autocatalytically maturing aspartic protease is pepsin.

18. The method according to claim 1 wherein said autocatalytically maturing aspartic protease is pepsin.

* * * * *

SEQUENCE LISTING

<160> NUMBER OF SEQ ID NOS: 23

<210> SEQ ID NO 1
<211> LENGTH: 1096
<212> TYPE: DNA
<213> ORGANISM: Artificial Sequence
<220> FEATURE:
<223> OTHER INFORMATION: GST-Pro-Hirudin fusion

<400> SEQUENCE: 1

```
atgtcccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240
atgttgggtg gttgtccaaa agagcgtgca gagatttcaa tgcttgaagg agcggttttg     300
gatattagat acgtgtttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg gatgcgttcc caaaattagt ttgttttaaa     540
aaacgtattg aagctatccc acaaattgat aagtacttga atccagcaa gtatatagca     600 tggccttttgc agggctggca agccacgttt ggtggtggcg accatcctcc aaaatcggat     660
ctggttccgc gtggatcccc gaattcccgg gtcgactcga gcggccgcgc tgagatcacc     720
aggatccctc tgtacaaagg caagtctctg aggaaggcgc tgaaggagca tgggcttctg     780
gaggacttcc tgcagaaaca gcagtatggc atcagcagca agtactccgg cttcgtcgtc     840
tataccgact gtaccgagtc cggtcagaac ctctgtctct gtgagggttc caacgtctgt     900
ggtcagggta acaagtgtat cctcggttcc gacggtgaga gaaccagtg tgtcaccggt     960 gagggaaccc caaagccaca gtcccacaac gacggtgact tgaggagat cccagaggag    1020 tatctccagt aaagatctaa gcttgctgct gctatcgaat tcctgcagcc cgggggatcc    1080
actagttcta gagcgg                                                   1096
```

<210> SEQ ID NO 2
<211> LENGTH: 343
<212> TYPE: PRT

<213> ORGANISM: Artificial Sequence
<220> FEATURE:
<223> OTHER INFORMATION: GST-Pro-Hirudin Fusion

<400> SEQUENCE: 2

| | | | | | | | | | | | | | | |
|---|---|---|---|---|---|---|---|---|---|---|---|---|---|---|
| Met | Ser | Pro | Ile | Leu | Gly | Tyr | Trp | Lys | Ile | Lys | Gly | Leu | Val | Gln | Pro |
| 1 | | | | 5 | | | | | 10 | | | | | 15 | |
| Thr | Arg | Leu | Leu | Leu | Glu | Tyr | Leu | Glu | Glu | Lys | Tyr | Glu | Glu | His | Leu |
| | | | 20 | | | | | 25 | | | | | 30 | | |
| Tyr | Glu | Arg | Asp | Glu | Gly | Asp | Lys | Trp | Arg | Asn | Lys | Lys | Phe | Glu | Leu |
| | | 35 | | | | | 40 | | | | | 45 | | | |
| Gly | Leu | Glu | Phe | Pro | Asn | Leu | Pro | Tyr | Tyr | Ile | Asp | Gly | Asp | Val | Lys |
| 50 | | | | | 55 | | | | | 60 | | | | | |
| Leu | Thr | Gln | Ser | Met | Ala | Ile | Ile | Arg | Tyr | Ile | Ala | Asp | Lys | His | Asn |
| 65 | | | | 70 | | | | | 75 | | | | | 80 | |
| Met | Leu | Gly | Gly | Cys | Pro | Lys | Glu | Arg | Ala | Glu | Ile | Ser | Met | Leu | Glu |
| | | | | 85 | | | | | 90 | | | | | 95 | |
| Gly | Ala | Val | Leu | Asp | Ile | Arg | Tyr | Gly | Val | Ser | Arg | Ile | Ala | Tyr | Ser |
| | | | 100 | | | | | 105 | | | | | 110 | | |
| Lys | Asp | Phe | Glu | Thr | Leu | Lys | Val | Asp | Phe | Leu | Ser | Lys | Leu | Pro | Glu |
| | | | 115 | | | | | 120 | | | | | 125 | | |
| Met | Leu | Lys | Met | Phe | Glu | Asp | Arg | Leu | Cys | His | Lys | Thr | Tyr | Leu | Asn |
| | 130 | | | | | 135 | | | | | 140 | | | | |
| Gly | Asp | His | Val | Thr | His | Pro | Asp | Phe | Met | Leu | Tyr | Asp | Ala | Leu | Asp |
| 145 | | | | | 150 | | | | | 155 | | | | | 160 |
| Val | Val | Leu | Tyr | Met | Asp | Pro | Met | Cys | Leu | Asp | Ala | Phe | Pro | Lys | Leu |
| | | | | 165 | | | | | 170 | | | | | 175 | |
| Val | Cys | Phe | Lys | Lys | Arg | Ile | Glu | Ala | Ile | Pro | Gln | Ile | Asp | Lys | Tyr |
| | | | 180 | | | | | 185 | | | | | 190 | | |
| Leu | Lys | Ser | Ser | Lys | Tyr | Ile | Ala | Trp | Pro | Leu | Gln | Gly | Trp | Gln | Ala |
| | | | 195 | | | | | 200 | | | | | 205 | | |
| Thr | Phe | Gly | Gly | Gly | Asp | His | Pro | Pro | Lys | Ser | Asp | Leu | Val | Pro | Arg |
| | 210 | | | | | 215 | | | | | 220 | | | | |
| Gly | Ser | Pro | Asn | Ser | Arg | Val | Asp | Ser | Ser | Gly | Arg | Ala | Glu | Ile | Thr |
| 225 | | | | | 230 | | | | | 235 | | | | | 240 |
| Arg | Ile | Pro | Leu | Tyr | Lys | Gly | Lys | Ser | Leu | Arg | Lys | Ala | Leu | Lys | Glu |
| | | | | 245 | | | | | 250 | | | | | 255 | |
| His | Gly | Leu | Leu | Glu | Asp | Phe | Leu | Gln | Lys | Gln | Tyr | Gly | Ile | Ser |
| | | | 260 | | | | | 265 | | | | | 270 | |
| Ser | Lys | Tyr | Ser | Gly | Phe | Val | Val | Tyr | Thr | Asp | Cys | Thr | Glu | Ser | Gly |
| | | 275 | | | | | 280 | | | | | 285 | | | |
| Gln | Asn | Leu | Cys | Leu | Cys | Glu | Gly | Ser | Asn | Val | Cys | Gly | Gln | Gly | Asn |
| | | 290 | | | | | 295 | | | | | 300 | | | |
| Lys | Cys | Ile | Leu | Gly | Ser | Asp | Gly | Glu | Lys | Asn | Gln | Cys | Val | Thr | Gly |
| 305 | | | | | 310 | | | | | 315 | | | | | 320 |
| Glu | Gly | Thr | Pro | Lys | Pro | Gln | Ser | His | Asn | Asp | Gly | Asp | Phe | Glu | Glu |
| | | | | 325 | | | | | 330 | | | | | 335 | |
| Ile | Pro | Glu | Glu | Tyr | Leu | Gln |
| | | | | 340 | | |

<210> SEQ ID NO 3
<211> LENGTH: 1119
<212> TYPE: DNA
<213> ORGANISM: Artificial Sequence
<220> FEATURE:
<223> OTHER INFORMATION: His-Pro-cGH

<400> SEQUENCE: 3

```
atgcggggtt ctcatcatca tcatcatcat ggtatggcta gcatgactgg tggacagcaa     60
atgggtcggg atctgtacga cgatgacgat aaggatccga gctcgagatc tgcagaaatc    120
ggatccgctg agatcaccag gatccctctg tacaaaggca agtctctgag gaaggcgctg    180
aaggagcatg gcttctggag gacttcctg cagaaacagc agtatggcat cagcagcaag    240
tactccggct ctcagacaa ccagcggctc ttcaataatg cagtcattcg tgtacaacac    300
ctgcaccagc tggctgcaaa aatgattaac gactttgagg acagcctgtt gcctgaggaa    360
cgcagacagc tgagtaaaat cttccctctg tctttctgca attctgacta cattgaggcg    420
cctgctggaa aagatgaaac acagaagagc tctatgctga gcttcttcg catctctttt    480
cacctcattg agtcctggga gttcccaagc cagtccctga gcggaaccgt ctcaaacagc    540
ctgaccgtag gaaccccaa ccagctcact gagaagctgg ccgacttgaa aatgggcatc    600
ctgcaccagc tggctgcaaa aatgattaac gactttgagg acagcctgtt gcctgaggaa    660
cgcagacagc tgagtaaaat cttccctctg tctttctgca attctgacta cattgaggcg    720
cctgctggaa aagatgaaac acagaagagc tctatgctga gcttcttcg catctctttt    780
cacctcattg agtcctggga gttcccaagc cagtccctga gcggaaccgt ctcaaacagc    840
ctgaccgtag gaaccccaa ccagctcact gagaagctgg ccgacttgaa aatgggcatc    900
agtgtgctca tccaggcatg tctcgatggt caaccaaaca tggatgataa cgactccttg    960
ccgctgcctt tgaggactt ctacttgacc atggggggaga caacctcag agagagcttt   1020
cgtctgctgg cttgcttcaa gaaggacatg cacaaagtcg agacctactt gagggttgca   1080
aattgcagga gatccctgga ttccaactgc accctgtag                          1119
```

<210> SEQ ID NO 4
<211> LENGTH: 388
<212> TYPE: PRT
<213> ORGANISM: Artificial Sequence
<220> FEATURE:
<223> OTHER INFORMATION: His-Pro-cGH

<400> SEQUENCE: 4

```
Met Arg Gly Ser His His His His His Gly Met Ala Ser Met Thr
 1               5                  10                  15

Gly Gly Gln Gln Met Gly Arg Asp Leu Thr Asp Asp Asp Lys Asp
                20                  25                  30

Pro Ser Ser Arg Ser Ala Glu Ile Gly Ser Ala Glu Ile Thr Arg Ile
            35                  40                  45

Pro Leu Tyr Lys Gly Lys Ser Leu Arg Lys Ala Leu Lys Glu His Gly
        50                  55                  60

Leu Leu Glu Asp Phe Leu Gln Lys Gln Gln Tyr Gly Ile Ser Ser Lys
65                  70                  75                  80

Tyr Ser Gly Phe Ser Asp Asn Gln Arg Leu Phe Asn Asn Ala Val Ile
                85                  90                  95

Arg Val Gln His Leu His Gln Leu Ala Ala Lys Met Ile Asn Asp Phe
            100                 105                 110

Glu Asp Ser Leu Leu Pro Glu Glu Arg Arg Gln Leu Ser Lys Ile Phe
        115                 120                 125

Pro Leu Ser Phe Cys Asn Ser Asp Tyr Ile Glu Ala Pro Ala Gly Lys
    130                 135                 140

Asp Glu Thr Gln Lys Ser Ser Met Leu Lys Leu Leu Arg Ile Ser Phe
```

-continued

```
                145                 150                 155                 160
His Leu Ile Glu Ser Trp Glu Phe Pro Ser Gln Ser Leu Ser Gly Thr
                165                 170                 175

Val Ser Asn Ser Leu Thr Val Gly Asn Pro Asn Gln Leu Thr Glu Lys
            180                 185                 190

Leu Ala Asp Leu Lys Met Gly Ile Ser Asp Asn Gln Arg Leu Phe Asn
        195                 200                 205

Asn Ala Val Ile Arg Val Gln His Leu His Gln Leu Ala Ala Lys Met
    210                 215                 220

Ile Asn Asp Phe Glu Asp Ser Leu Leu Pro Glu Glu Arg Arg Gln Leu
225                 230                 235                 240

Ser Lys Ile Phe Pro Leu Ser Phe Cys Asn Ser Asp Tyr Ile Glu Ala
                245                 250                 255

Pro Ala Gly Lys Asp Glu Thr Gln Lys Ser Ser Met Leu Lys Leu Leu
            260                 265                 270

Arg Ile Ser Phe His Leu Ile Glu Ser Trp Glu Phe Pro Ser Gln Ser
        275                 280                 285

Leu Ser Gly Thr Val Ser Asn Ser Leu Thr Val Gly Asn Pro Asn Gln
    290                 295                 300

Leu Thr Glu Lys Leu Ala Asp Leu Lys Met Gly Ile Ser Val Leu Ile
305                 310                 315                 320

Gln Ala Cys Leu Asp Gly Gln Pro Asn Met Asp Asp Asn Asp Ser Leu
                325                 330                 335

Pro Leu Pro Phe Glu Asp Phe Tyr Leu Thr Met Gly Glu Asn Asn Leu
            340                 345                 350

Arg Glu Ser Phe Arg Leu Leu Ala Cys Phe Lys Lys Asp Met His Lys
        355                 360                 365

Val Glu Thr Tyr Leu Arg Val Ala Asn Cys Arg Arg Ser Leu Asp Ser
    370                 375                 380

Asn Cys Thr Leu
385

<210> SEQ ID NO 5
<211> LENGTH: 42
<212> TYPE: PRT
<213> ORGANISM: Calf

<400> SEQUENCE: 5

Ala Glu Ile Thr Arg Ile Pro Leu Tyr Lys Gly Lys Ser Leu Arg Lys
1               5                   10                  15

Ala Leu Lys Glu His Gly Leu Leu Glu Asp Phe Leu Gln Lys Gln Gln
            20                  25                  30

Tyr Gly Ile Ser Ser Lys Tyr Ser Gly Phe
        35                  40

<210> SEQ ID NO 6
<211> LENGTH: 39
<212> TYPE: PRT
<213> ORGANISM: Artificial Sequence
<220> FEATURE:
<223> OTHER INFORMATION: KLIP4

<400> SEQUENCE: 6

Ala Glu Ile Thr Arg Ile Pro Leu Tyr Lys Gly Lys Ser Leu Arg Lys
1               5                   10                  15

Ala Leu Lys Glu His Gly Leu Leu Glu Asp Phe Leu Gln Lys Gln Gln
            20                  25                  30
```

```
Tyr Gly Ile Ser Ser Lys Phe
        35

<210> SEQ ID NO 7
<211> LENGTH: 28
<212> TYPE: PRT
<213> ORGANISM: Artificial Sequence
<220> FEATURE:
<223> OTHER INFORMATION: KLIP11

<400> SEQUENCE: 7

Lys Ser Leu Arg Lys Ala Leu Lys Glu His Gly Leu Leu Glu Asp Phe
1               5                   10                  15

Leu Gln Lys Gln Gln Tyr Gly Ile Ser Ser Lys Phe
            20                  25

<210> SEQ ID NO 8
<211> LENGTH: 21
<212> TYPE: PRT
<213> ORGANISM: Artificial Sequence
<220> FEATURE:
<223> OTHER INFORMATION: KLIP12

<400> SEQUENCE: 8

Lys Glu His Gly Leu Leu Glu Asp Phe Leu Gln Lys Gln Gln Tyr Gly
1               5                   10                  15

Ile Ser Ser Lys Phe
            20

<210> SEQ ID NO 9
<211> LENGTH: 12
<212> TYPE: PRT
<213> ORGANISM: Artificial Sequence
<220> FEATURE:
<223> OTHER INFORMATION: KLIP14

<400> SEQUENCE: 9

Leu Gln Lys Gln Gln Tyr Gly Ile Ser Ser Lys Phe
1               5                   10

<210> SEQ ID NO 10
<211> LENGTH: 6
<212> TYPE: PRT
<213> ORGANISM: Artificial Sequence
<220> FEATURE:
<223> OTHER INFORMATION: KLIP15

<400> SEQUENCE: 10

Gly Ile Ser Ser Lys Phe
1               5

<210> SEQ ID NO 11
<211> LENGTH: 2
<212> TYPE: PRT
<213> ORGANISM: Artificial Sequence
<220> FEATURE:
<223> OTHER INFORMATION: KLIP16

<400> SEQUENCE: 11

Gly Arg
1

<210> SEQ ID NO 12
<211> LENGTH: 1134
<212> TYPE: DNA
```

<210> SEQ ID NO 12
<211> LENGTH: 1134
<212> TYPE: DNA
<213> ORGANISM: Artificial Sequence
<220> FEATURE:
<223> OTHER INFORMATION: GST-KLIP4-cystatin

<400> SEQUENCE: 12

```
atgtcccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg agtttcccaa tcttcctta tatattgat      180
ggtgatgtta aattaacaca gtctatggcc atcatacgtt atatagctga caagcacaac     240
atgttgggtg gttgtccaaa agagcgtgca gagatttcaa tgcttgaagg agcggttttg     300
gatattagat acggtgtttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg atgcgttcc caaaattagt ttgttttaaa      540
aaacgtattg aagctatccc acaaattgat aagtacttga atccagcaa gtatatagca     600
tggcctttgc agggctggca agccacgttt ggtggtggcg accatcctcc aaaatcggat     660
ctggttccgc gtggatcccc gaattcccgg tcgactcga gcggccgcgc tgagatcacc     720
aggatccctc tgtacaaagg caagtctctg aggaaggcgc tgaaggagca tgggcttctg     780
gaggacttcc tgcagaaaca gcagtatggc atcagcagca agttcatgtc gagcgacgga     840
gggccggtgc ttggcggcgt cgagccggtg gggaacgaga cgacctcca cctcgtcgac     900
ctcgcccgct cgccgtcac cgagcacaac aagaaggcca attctctgct ggagttcgag     960
aagcttgtga gtgtgaagca gcaagttgtc gctggcactt tgtactattt cacaattgag    1020
gtgaaggaag gggatgccaa gaagctctat gaagctaagg tctgggagaa accatggatg    1080
gacttcaagg agctccagga gttcaagcct gtcgatgcca gtgcaaatgc ctaa          1134
```

<210> SEQ ID NO 13
<211> LENGTH: 377
<212> TYPE: PRT
<213> ORGANISM: Artificial Sequence
<220> FEATURE:
<223> OTHER INFORMATION: GST-KLIP4-cystatin

<400> SEQUENCE: 13

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
```

```
                130                 135                 140
Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Asn Ser Arg Val Asp Ser Ser Gly Arg Ala Glu Ile Thr
225                 230                 235                 240

Arg Ile Pro Leu Tyr Lys Gly Lys Ser Leu Arg Lys Ala Leu Lys Glu
                245                 250                 255

His Gly Leu Leu Glu Asp Phe Leu Gln Lys Gln Tyr Gly Ile Ser
            260                 265                 270

Ser Lys Phe Met Ser Ser Asp Gly Gly Pro Val Leu Gly Gly Val Glu
        275                 280                 285

Pro Val Gly Asn Glu Asn Asp Leu His Leu Val Asp Leu Ala Arg Phe
    290                 295                 300

Ala Val Thr Glu His Asn Lys Lys Ala Asn Ser Leu Leu Glu Phe Glu
305                 310                 315                 320

Lys Leu Val Ser Val Lys Gln Gln Val Val Ala Gly Thr Leu Tyr Tyr
                325                 330                 335

Phe Thr Ile Glu Val Lys Glu Gly Asp Ala Lys Lys Leu Tyr Glu Ala
            340                 345                 350

Lys Val Trp Glu Lys Pro Trp Met Asp Phe Lys Glu Leu Gln Glu Phe
        355                 360                 365

Lys Pro Val Asp Ala Ser Ala Asn Ala
    370                 375

<210> SEQ ID NO 14
<211> LENGTH: 1101
<212> TYPE: DNA
<213> ORGANISM: Artificial Sequence
<220> FEATURE:
<223> OTHER INFORMATION: GST-KLIP11-cystatin

<400> SEQUENCE: 14
atgtccccta tactaggtta ttggaaaatt aagggccttg tgcaacccac tcgacttctt    60
ttggaatatc ttgaagaaaa atatgaagag catttgtatg agcgcgatga aggtgataaa   120
tggcgaaaca aaaagtttga attgggtttg agtttcccca tcttccttta ttatattgat   180
ggtgatgtta aattaacaca gtctatggcc atcatacgtt atatagctga caagcacaac   240
atgttgggtg ttgtccaaa agagcgtgca gagatttcaa tgcttgaagg agcggttttg   300
gatattagat acggtgtttc gagaattgca tatagtaaag actttgaaac tctcaaagtt   360
gattttctta gcaagctacc tgaaatgctg aaaatgttcg aagatcgttt atgtcataaa   420
acatatttaa atggtgatca tgtaacccat cctgacttca tgttgtatga cgctcttgat   480 gttgtttat acatggaccc aatgtgcctg gatgcgttcc caaaattagt ttgttttaaa   540
aaacgtattg aagctatccc acaaattgat aagtacttga atccagcaa gtatatagca   600 tggcctttgc agggctggca agccacgttt ggtggtggcg accatcctcc aaaatcggat   660
```

-continued

```
ctggttccgc gtggatcccc gaattcccgg gtcgactcga gcggccgcaa gtctctgagg    720
aaggcgctga aggagcatgg gcttctggag gacttcctgc agaaacagca gtatggcatc    780
agcagcaagt tcatgtcgag cgacggaggg ccggtgcttg gcggcgtcga gccggtgggg    840
aacgagaacg acctccacct cgtcgacctc gcccgcttcg ccgtcaccga gcacaacaag    900
aaggccaatt ctctgctgga gttcgagaag cttgtgagtg tgaagcagca agttgtcgct    960
ggcactttgt actatttcac aattgaggtg aaggaagggg atgccaagaa gctctatgaa   1020
gctaaggtct gggagaaacc atggatggac ttcaaggagc tccaggagtt caagcctgtc   1080
gatgccagtg caaatgccta a                                              1101
```

<210> SEQ ID NO 15
<211> LENGTH: 366
<212> TYPE: PRT
<213> ORGANISM: Artificial Sequence
<220> FEATURE:
<223> OTHER INFORMATION: GST-KLIP11-cystatin

<400> SEQUENCE: 15

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Asn Ser Arg Val Asp Ser Ser Gly Arg Lys Ser Leu Arg
225                 230                 235                 240

Lys Ala Leu Lys Glu His Gly Leu Leu Glu Asp Phe Leu Gln Lys Gln
                245                 250                 255

Gln Tyr Gly Ile Ser Ser Lys Phe Met Ser Ser Asp Gly Gly Pro Val
            260                 265                 270

Leu Gly Gly Val Glu Pro Val Gly Asn Glu Asn Asp Leu His Leu Val
        275                 280                 285
```

```
Asp Leu Ala Arg Phe Ala Val Thr Glu His Asn Lys Lys Ala Asn Ser
        290                 295                 300

Leu Leu Glu Phe Glu Lys Leu Val Ser Val Lys Gln Gln Val Val Ala
305                 310                 315                 320

Gly Thr Leu Tyr Tyr Phe Thr Ile Glu Val Lys Glu Gly Asp Ala Lys
                325                 330                 335

Lys Leu Tyr Glu Ala Lys Val Trp Glu Lys Pro Trp Met Asp Phe Lys
            340                 345                 350

Glu Leu Gln Glu Phe Lys Pro Val Asp Ala Ser Ala Asn Ala
        355                 360                 365

<210> SEQ ID NO 16
<211> LENGTH: 1080
<212> TYPE: DNA
<213> ORGANISM: Artificial Sequence
<220> FEATURE:
<223> OTHER INFORMATION: GST-KLIP12-cystatin

<400> SEQUENCE: 16
atgtccccta tactaggtta ttggaaaatt aagggccttg tgcaacccac tcgacttctt    60
ttggaatatc ttgaagaaaa atatgaagag catttgtatg agcgcgatga aggtgataaa   120
tggcgaaaca aaaagtttga attgggtttg agtttcccaa tcttcctta ttatattgat    180
ggtgatgtta aattaacaca gtctatggcc atcatacgtt atatagctga caagcacaac   240
atgttgggtg ttgtccaaa agagcgtgca gagatttcaa tgcttgaagg agcggttttg   300
gatattagat acggtgtttc gagaattgca tatagtaaag actttgaaac tctcaaagtt   360
gatttttctta gcaagctacc tgaaatgctg aaaatgttcg aagatcgttt atgtcataaa   420
acatatttaa atggtgatca tgtaacccat cctgacttca tgttgtatga cgctcttgat   480
gttgttttat acatggaccc aatgtgcctg atgcgttcc caaaattagt ttgttttaaa   540
aaacgtattg aagctatccc acaaattgat aagtacttga atccagcaa gtatatagca   600
tggcctttgc agggctggca agccacgttt ggtggtggcg accatcctcc aaaatcggat   660
ctggttccgc gtggatcccc gaattcccgg tcgactcga gcggccgcaa ggagcatggg   720
cttctggagg acttcctgca gaaacagcag tatggcatca gcagcaagtt catgtcgagc   780
gacggagggc cggtgcttgg cggcgtcgag ccggtgggga cgagaacga cctccacctc   840
gtcgacctcg cccgcttcgc cgtcaccgag cacaacaaga aggccaattc tctgctggag   900
ttcgagaagc ttgtgagtgt gaagcagcaa gttgtcgctg cactttgta ctatttcaca   960
attgaggtga aggaaggga tgccaagaag ctctatgaag ctaaggtctg gagaaaccat  1020
ggatggact tcaaggagct ccaggagttc aagcctgtcg atgccagtgc aaatgcctaa  1080

<210> SEQ ID NO 17
<211> LENGTH: 359
<212> TYPE: PRT
<213> ORGANISM: Artificial Sequence
<220> FEATURE:
<223> OTHER INFORMATION: GST-KLIP12-cystatin

<400> SEQUENCE: 17

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
```

```
                35                  40                  45
Gly Leu Glu Phe Pro Asn Leu Pro Tyr Tyr Ile Asp Gly Asp Val Lys
 50                  55                  60
Leu Thr Gln Ser Met Ala Ile Ile Arg Tyr Ile Ala Asp Lys His Asn
 65                  70                  75                  80
Met Leu Gly Gly Cys Pro Lys Glu Arg Ala Glu Ile Ser Met Leu Glu
                 85                  90                  95
Gly Ala Val Leu Asp Ile Arg Tyr Gly Val Ser Arg Ile Ala Tyr Ser
                100                 105                 110
Lys Asp Phe Glu Thr Leu Lys Val Asp Phe Leu Ser Lys Leu Pro Glu
            115                 120                 125
Met Leu Lys Met Phe Glu Asp Arg Leu Cys His Lys Thr Tyr Leu Asn
130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
            180                 185                 190
Leu Lys Ser Ser Lys Tyr Ile Ala Trp Pro Leu Gln Gly Trp Gln Ala
        195                 200                 205
Thr Phe Gly Gly Gly Asp His Pro Pro Lys Ser Asp Leu Val Pro Arg
    210                 215                 220
Gly Ser Pro Asn Ser Arg Val Asp Ser Ser Gly Arg Lys Glu His Gly
225                 230                 235                 240
Leu Leu Glu Asp Phe Leu Gln Lys Gln Gln Tyr Gly Ile Ser Ser Lys
                245                 250                 255
Phe Met Ser Ser Asp Gly Gly Pro Val Leu Gly Gly Val Glu Pro Val
            260                 265                 270
Gly Asn Glu Asn Asp Leu His Leu Val Asp Leu Ala Arg Phe Ala Val
        275                 280                 285
Thr Glu His Asn Lys Lys Ala Asn Ser Leu Leu Glu Phe Glu Lys Leu
    290                 295                 300
Val Ser Val Lys Gln Gln Val Val Ala Gly Thr Leu Tyr Tyr Phe Thr
305                 310                 315                 320
Ile Glu Val Lys Glu Gly Asp Ala Lys Lys Leu Tyr Glu Ala Lys Val
                325                 330                 335
Trp Glu Lys Pro Trp Met Asp Phe Lys Glu Leu Gln Glu Phe Lys Pro
            340                 345                 350
Val Asp Ala Ser Ala Asn Ala
        355

<210> SEQ ID NO 18
<211> LENGTH: 1053
<212> TYPE: DNA
<213> ORGANISM: Artificial Sequence
<220> FEATURE:
<223> OTHER INFORMATION: GST-KLIP14-cystatin

<400> SEQUENCE: 18
atgtccccta ctactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240
```

-continued

```
atgttgggtg gttgtccaaa agagcgtgca gagatttcaa tgcttgaagg agcggttttg    300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg atgcgttcc caaaattagt ttgttttaaa     540
aaacgtattg aagctatccc acaaattgat aagtacttga atccagcaa gtatatagca    600
tggcctttgc agggctggca agccacgttt ggtggtggcg accatcctcc aaaatcggat    660
ctggttccgc gtggatcccc gaattcccgg tcgactcga gcggccgcct gcagaaacag    720
cagtatggca tcagcagcaa gttcatgtcg agcgacggag ggccggtgct tggcggcgtc    780
gagccggtgg ggaacgagaa cgacctccac ctcgtcgacc tcgcccgctt cgccgtcacc    840
gagcacaaca agaaggccaa ttctctgctg gagttcgaga agcttgtgag tgtgaagcag    900
caagttgtcg ctggcacttt gtactatttc acaattgagg tgaaggaagg ggatgccaag    960
aagctctatg aagctaaggt ctgggagaaa ccatggatgg acttcaagga gctccaggag   1020
ttcaagcctg tcgatgccag tgcaaatgcc taa                                1053
```

<210> SEQ ID NO 19
<211> LENGTH: 350
<212> TYPE: PRT
<213> ORGANISM: Artificial Sequence
<220> FEATURE:
<223> OTHER INFORMATION: GST-KLIP14-cystatin

<400> SEQUENCE: 19

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
```

-continued

```
           210                 215                 220
Gly Ser Pro Asn Ser Arg Val Asp Ser Ser Gly Arg Leu Gln Lys Gln
225                 230                 235                 240

Gln Tyr Gly Ile Ser Ser Lys Phe Met Ser Ser Asp Gly Gly Pro Val
                245                 250                 255

Leu Gly Gly Val Glu Pro Val Gly Asn Glu Asn Asp Leu His Leu Val
            260                 265                 270

Asp Leu Ala Arg Phe Ala Val Thr Glu His Asn Lys Lys Ala Asn Ser
        275                 280                 285

Leu Leu Glu Phe Glu Lys Leu Val Ser Val Lys Gln Gln Val Val Ala
    290                 295                 300

Gly Thr Leu Tyr Tyr Phe Thr Ile Glu Val Lys Glu Gly Asp Ala Lys
305                 310                 315                 320

Lys Leu Tyr Glu Ala Lys Val Trp Glu Lys Pro Trp Met Asp Phe Lys
                325                 330                 335

Glu Leu Gln Glu Phe Lys Pro Val Asp Ala Ser Ala Asn Ala
            340                 345                 350
```

<210> SEQ ID NO 20
<211> LENGTH: 1035
<212> TYPE: DNA
<213> ORGANISM: Artificial Sequence
<220> FEATURE:
<223> OTHER INFORMATION: GST-KLIP15-cystatin

<400> SEQUENCE: 20

```
atgtcccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240
atgttgggtg ttgtccaaa agagcgtgca gagatttcaa tgcttgaagg agcggttttg     300
gatattagat acgtgtttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg atgcgttcc aaaattagt ttgttttaaa     540
aaacgtattg aagctatccc acaaattgat aagtacttga atccagcaa gtatatagca     600
tggcctttgc agggctggca agccacgttt ggtggtggcg accatcctcc aaaatcggat     660
ctggttccgc gtggatcccc gaattcccgg tcgactcga gcggccgcgg catcagcagc     720
aagttcatgt cgagcgacgg agggccggtg cttggcggcg tcgagccggt ggggaacgag     780
aacgacctcc acctcgtcga cctcgcccgc ttcgccgtca ccgagcacaa caagaaggcc     840
aattctctgc tggagttcga gaagcttgtg agtgtgaagc agcaagttgt cgctggcact     900
ttgtactatt tcacaattga ggtgaaggaa ggggatgcca agaagctcta tgaagctaag     960
gtctgggaga aaccatggat ggacttcaag gagctccagg agttcaagcc tgtcgatgcc    1020
agtgcaaatg cctaa                                                     1035
```

<210> SEQ ID NO 21
<211> LENGTH: 344
<212> TYPE: PRT
<213> ORGANISM: Artificial Sequence
<220> FEATURE:
<223> OTHER INFORMATION: GST-KLIP15-cystatin

<400> SEQUENCE: 21

| Met | Ser | Pro | Ile | Leu | Gly | Tyr | Trp | Lys | Ile | Lys | Gly | Leu | Val | Gln | Pro |
|---|---|---|---|---|---|---|---|---|---|---|---|---|---|---|---|
| 1 | | | | 5 | | | | | 10 | | | | | 15 | |

| Thr | Arg | Leu | Leu | Leu | Glu | Tyr | Leu | Glu | Glu | Lys | Tyr | Glu | Glu | His | Leu |
|---|---|---|---|---|---|---|---|---|---|---|---|---|---|---|---|
| | | | | 20 | | | | | 25 | | | | | 30 | |

| Tyr | Glu | Arg | Asp | Glu | Gly | Asp | Lys | Trp | Arg | Asn | Lys | Lys | Phe | Glu | Leu |
|---|---|---|---|---|---|---|---|---|---|---|---|---|---|---|---|
| | | | 35 | | | | | 40 | | | | | 45 | | |

| Gly | Leu | Glu | Phe | Pro | Asn | Leu | Pro | Tyr | Tyr | Ile | Asp | Gly | Asp | Val | Lys |
|---|---|---|---|---|---|---|---|---|---|---|---|---|---|---|---|
| | 50 | | | | | 55 | | | | | 60 | | | | |

| Leu | Thr | Gln | Ser | Met | Ala | Ile | Ile | Arg | Tyr | Ile | Ala | Asp | Lys | His | Asn |
|---|---|---|---|---|---|---|---|---|---|---|---|---|---|---|---|
| 65 | | | | | 70 | | | | | 75 | | | | | 80 |

| Met | Leu | Gly | Gly | Cys | Pro | Lys | Glu | Arg | Ala | Glu | Ile | Ser | Met | Leu | Glu |
|---|---|---|---|---|---|---|---|---|---|---|---|---|---|---|---|
| | | | | 85 | | | | | 90 | | | | | 95 | |

| Gly | Ala | Val | Leu | Asp | Ile | Arg | Tyr | Gly | Val | Ser | Arg | Ile | Ala | Tyr | Ser |
|---|---|---|---|---|---|---|---|---|---|---|---|---|---|---|---|
| | | | 100 | | | | | 105 | | | | | 110 | | |

| Lys | Asp | Phe | Glu | Thr | Leu | Lys | Val | Asp | Phe | Leu | Ser | Lys | Leu | Pro | Glu |
|---|---|---|---|---|---|---|---|---|---|---|---|---|---|---|---|
| | | | 115 | | | | | 120 | | | | | 125 | | |

| Met | Leu | Lys | Met | Phe | Glu | Asp | Arg | Leu | Cys | His | Lys | Thr | Tyr | Leu | Asn |
|---|---|---|---|---|---|---|---|---|---|---|---|---|---|---|---|
| | 130 | | | | | 135 | | | | | 140 | | | | |

| Gly | Asp | His | Val | Thr | His | Pro | Asp | Phe | Met | Leu | Tyr | Asp | Ala | Leu | Asp |
|---|---|---|---|---|---|---|---|---|---|---|---|---|---|---|---|
| 145 | | | | | 150 | | | | | 155 | | | | | 160 |

| Val | Val | Leu | Tyr | Met | Asp | Pro | Met | Cys | Leu | Asp | Ala | Phe | Pro | Lys | Leu |
|---|---|---|---|---|---|---|---|---|---|---|---|---|---|---|---|
| | | | | 165 | | | | | 170 | | | | | 175 | |

| Val | Cys | Phe | Lys | Lys | Arg | Ile | Glu | Ala | Ile | Pro | Gln | Ile | Asp | Lys | Tyr |
|---|---|---|---|---|---|---|---|---|---|---|---|---|---|---|---|
| | | | 180 | | | | | 185 | | | | | 190 | | |

| Leu | Lys | Ser | Ser | Lys | Tyr | Ile | Ala | Trp | Pro | Leu | Gln | Gly | Trp | Gln | Ala |
|---|---|---|---|---|---|---|---|---|---|---|---|---|---|---|---|
| | | | 195 | | | | | 200 | | | | | 205 | | |

| Thr | Phe | Gly | Gly | Gly | Asp | His | Pro | Pro | Lys | Ser | Asp | Leu | Val | Pro | Arg |
|---|---|---|---|---|---|---|---|---|---|---|---|---|---|---|---|
| | 210 | | | | | 215 | | | | | 220 | | | | |

| Gly | Ser | Pro | Asn | Ser | Arg | Val | Asp | Ser | Ser | Gly | Arg | Gly | Ile | Ser | Ser |
|---|---|---|---|---|---|---|---|---|---|---|---|---|---|---|---|
| 225 | | | | | 230 | | | | | 235 | | | | | 240 |

| Lys | Phe | Met | Ser | Ser | Asp | Gly | Gly | Pro | Val | Leu | Gly | Gly | Val | Glu | Pro |
|---|---|---|---|---|---|---|---|---|---|---|---|---|---|---|---|
| | | | | 245 | | | | | 250 | | | | | 255 | |

| Val | Gly | Asn | Glu | Asn | Asp | Leu | His | Leu | Val | Asp | Leu | Ala | Arg | Phe | Ala |
|---|---|---|---|---|---|---|---|---|---|---|---|---|---|---|---|
| | | | 260 | | | | | 265 | | | | | 270 | | |

| Val | Thr | Glu | His | Asn | Lys | Lys | Ala | Asn | Ser | Leu | Leu | Glu | Phe | Glu | Lys |
|---|---|---|---|---|---|---|---|---|---|---|---|---|---|---|---|
| | | | 275 | | | | | 280 | | | | | 285 | | |

| Leu | Val | Ser | Val | Lys | Gln | Gln | Val | Val | Ala | Gly | Thr | Leu | Tyr | Tyr | Phe |
|---|---|---|---|---|---|---|---|---|---|---|---|---|---|---|---|
| | 290 | | | | | 295 | | | | | 300 | | | | |

| Thr | Ile | Glu | Val | Lys | Glu | Gly | Asp | Ala | Lys | Lys | Leu | Tyr | Glu | Ala | Lys |
|---|---|---|---|---|---|---|---|---|---|---|---|---|---|---|---|
| 305 | | | | | 310 | | | | | 315 | | | | | 320 |

| Val | Trp | Glu | Lys | Pro | Trp | Met | Asp | Phe | Lys | Glu | Leu | Gln | Glu | Phe | Lys |
|---|---|---|---|---|---|---|---|---|---|---|---|---|---|---|---|
| | | | | 325 | | | | | 330 | | | | | 335 | |

| Pro | Val | Asp | Ala | Ser | Ala | Asn | Ala |
|---|---|---|---|---|---|---|---|
| | | | 340 | | | | |

<210> SEQ ID NO 22
<211> LENGTH: 1017
<212> TYPE: DNA
<213> ORGANISM: Artificial Sequence
<220> FEATURE:
<223> OTHER INFORMATION: GST-KLIP16-cystatin

<400> SEQUENCE: 22

```
atgtcccta tactaggtta ttggaaaatt aagggccttg tgcaacccac tcgacttctt    60
ttggaatatc ttgaagaaaa atatgaagag catttgtatg agcgcgatga aggtgataaa   120
tggcgaaaca aaaagtttga attgggtttg gagtttccca atcttcctta ttatattgat   180
ggtgatgtta aattaacaca gtctatggcc atcatacgtt atatagctga caagcacaac   240
atgttgggtg gttgtccaaa agagcgtgca gagatttcaa tgcttgaagg agcggttttg   300
gatattagat acggtgtttc gagaattgca atagtaaag actttgaaac tctcaaagtt    360
gattttctta gcaagctacc tgaaatgctg aaaatgttcg aagatcgttt atgtcataaa   420
acatatttaa atggtgatca tgtaacccat cctgacttca tgttgtatga cgctcttgat   480
gttgttttat acatggaccc aatgtgcctg gatgcgttcc caaaattagt ttgttttaaa   540
aaacgtattg aagctatccc acaaattgat aagtacttga atccagcaa gtatatagca    600
tggcctttgc agggctggca agccacgttt ggtggtggcg accatcctcc aaaatcggat   660
ctggttccgc gtggatcccc gaattcccgg gtcgactcga gcggccgcat gtcgagcgac   720
ggagggccgg tgcttggcgg cgtcgagccg gtggggaacg agaacgacct ccacctcgtc   780
gacctcgccc gcttcgccgt caccgagcac aacaagaagg ccaattctct gctggagttc   840
gagaagcttg tgagtgtgaa gcagcaagtt gtcgctggca ctttgtacta tttcacaatt   900
gaggtgaagg aagggatgc caagaagctc tatgaagcta aggtctggga gaaaccatgg   960
atggacttca aggagctcca ggagttcaag cctgtcgatg ccagtgcaaa tgcctaa    1017
```

<210> SEQ ID NO 23
<211> LENGTH: 338
<212> TYPE: PRT
<213> ORGANISM: Artificial Sequence
<220> FEATURE:
<223> OTHER INFORMATION: GST-KLIP16-cystatin

<400> SEQUENCE: 23

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190
```

```
Leu Lys Ser Ser Lys Tyr Ile Ala Trp Pro Leu Gln Gly Trp Gln Ala
        195             200             205
Thr Phe Gly Gly Gly Asp His Pro Pro Lys Ser Asp Leu Val Pro Arg
        210             215             220
Gly Ser Pro Asn Ser Arg Val Asp Ser Ser Gly Arg Met Ser Ser Asp
225                 230             235             240
Gly Gly Pro Val Leu Gly Gly Val Glu Pro Val Gly Asn Glu Asn Asp
                245             250             255
Leu His Leu Val Asp Leu Ala Arg Phe Ala Val Thr Glu His Asn Lys
                260             265             270
Lys Ala Asn Ser Leu Leu Glu Phe Glu Lys Leu Val Ser Val Lys Gln
        275             280             285
Gln Val Val Ala Gly Thr Leu Tyr Tyr Phe Thr Ile Glu Val Lys Glu
        290             295             300
Gly Asp Ala Lys Lys Leu Tyr Glu Ala Lys Val Trp Glu Lys Pro Trp
305             310             315             320
Met Asp Phe Lys Glu Leu Gln Glu Phe Lys Pro Val Asp Ala Ser Ala
                325             330             335
Asn Ala
```